(12) United States Patent
Shull et al.

(10) Patent No.: US 8,722,864 B2
(45) Date of Patent: May 13, 2014

(54) GLYCOSYLATED ACETAMINOPHEN PRO-DRUG ANALOGS

(75) Inventors: Brian Shull, Durham, NC (US); John Baldwin, Gwynedd, PA (US); Ramesh Gopalaswamy, Cary, NC (US); Zishan Haroon, Chapel Hill, NC (US)

(73) Assignee: Nutek Pharma Ltd., Chapel Hill, NC (US)

( * ) Notice: Subject to any disclaimer, the term of this patent is extended or adjusted under 35 U.S.C. 154(b) by 236 days.

(21) Appl. No.: 13/183,222

(22) Filed: Jul. 14, 2011

(65) Prior Publication Data

US 2012/0022012 A1    Jan. 26, 2012

Related U.S. Application Data

(60) Provisional application No. 61/366,729, filed on Jul. 22, 2010.

(51) Int. Cl.
*C07H 15/203* (2006.01)
(52) U.S. Cl.
CPC .................................. *C07H 15/203* (2013.01)
USPC .......................................... 536/17.9; 514/25
(58) Field of Classification Search
None
See application file for complete search history.

(56) References Cited

U.S. PATENT DOCUMENTS 5,760,008 A * 6/1998 Rubin ............................. 514/25
7,033,800 B2 * 4/2006 Okada et al. .................... 435/74

OTHER PUBLICATIONS

Boschi et al., "Effect of "carrier" sugar on analgesic activity: glycosides of common analgesics" European Journal of Medicinal Chemistry (1981) vol. 16 No. 2 pp. 125-130.*
Boschi et al., "Influence du 'vecteur' sucre sur l'active antaligique: glycosides d'analgesiques usuels" European Journal of Medicinal Chemistry—Chimica Therapeutica (1981) vol. 16 No. 2 pp. 125-130.*
Ekborg et al., "Synthesis of p-Nitrophenyl 4-O-(alpha-D-Mannopyranosyl)-alpha-L-rhamnoside and p-Acetamidophenyl 4-O-(beta-D-Mannopyranosyl)-alpha-L-rhamnoside" Acta Chemica Scandinavica B (1975) vol. 29 pp. 1031-1035.*

* cited by examiner

*Primary Examiner* — Eric S Olson
(74) *Attorney, Agent, or Firm* — Medlen & Carroll, LLP

(57) ABSTRACT

The present invention relates to methods and compositions for the synthesis, production, and use of pro-drug analogs of the analgesic acetaminophen. This invention relates to a method for the production of a broad group of glycosides of acetaminophen derivatives.

16 Claims, 20 Drawing Sheets effect on oxidation and de-acylation?

relative stability to dilute acidic formulation relative water solubility

Analog from the 1997 patent
little water solubility

Current analog with
high water solubility

GLYCOSYLATED ACETAMINOPHEN PRO-DRUG ANALOGS

This application claims benefit of provisional application 61/366,729, filed Jul. 22, 2010.

FIELD OF THE INVENTION

The present invention relates to methods and compositions for the production and use of pro-drug analogs of the analgesic acetaminophen. This invention relates to a method for the production of a broad group of novel glycoside derivatives of acetaminophen. The invention also importantly relates to the resulting glycosides as novel compounds of diverse application having desired properties including pharmacodynamic properties; and to medicaments containing the pro-drug compounds.

BACKGROUND OF THE INVENTION

Acetaminophen is a widely used over-the-counter analgesic (pain reliever) and antipyretic (fever reducer). It is commonly used for the relief of fever, headaches, and other minor aches and pains, and is a major ingredient in numerous cold and flu remedies. In combination with non-steroidal anti-inflammatory drugs (NSAIDs) and opioid analgesics, acetaminophen is used also in the management of more severe pain (such as postoperative pain).

One of the problems in the development of an injectable acetaminophen is its poor solubility in water. One approach to improve solubility is to glycosylate acetaminophen. For example, glycosylated acetaminophen pro-drug analogs that with an olefin at the 2,3 position of the carbohydrate are described in U.S. Pat. No. 5,693,767 [1] shown in FIG. 1.

Acetaminophen is most stable at pH 6, and the analogs with the olefin at the 2,3 position, will hydrolyze easily at this and lower pH's. Thus, new acetaminophen analogs that are more stable to pH's lower than 7 are needed.

SUMMARY OF THE INVENTION

In one embodiment, the invention relates to a pro-drug 2,3-hydroxy-glycoside derivative of acetaminophen, methods of making the same, and methods for administering the same to a subject. In one embodiment, the invention relates to a compound of the formula:

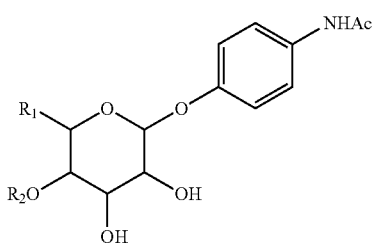

wherein $R_1$ is an alkyl, alkyl alkanoate, alkenyl, alkynyl, acyl, alkanediyl, aryl, aralkyl, heteroaryl, heteroaralkyl, alkyl oximes (R=CH=NOH), alkyl hydrazones (R=CH=NHNHR), alkyl amines, or a substituted version of any of these groups or a protecting group, phosphates [R=—OP(O)(OH)$_2$]v, sulfonates [R=OS(O)$_2$OH], sugar, OH, or H; and $R_2$ is an alkyl, alkyl alkanoate, alkenyl, alkynyl, acyl, alkanediyl, aryl, aralkyl, heteroaryl, heteroaralkyl, alkyl oximes (R=CH=NOH), alkyl hydrazones (R=CH=NHNHR), alkyl amines or a substituted version of any of these groups or a protecting group, phosphates [R=—OP(O)(OH)$_2$], sulfonates [R=OS(O)$_2$OH], sugar, or H. In one embodiment, said compound comprises a monosaccharide derivative of acetaminophen. In one embodiment, said compound comprises disaccharide derivative of acetaminophen. In one embodiment, said compound, further comprising a pharmaceutically effective carrier. In one embodiment, the invention relates to a compound of the formula:

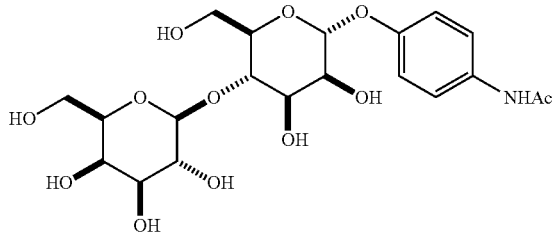

In one embodiment, the invention relates to a compound of the formula:

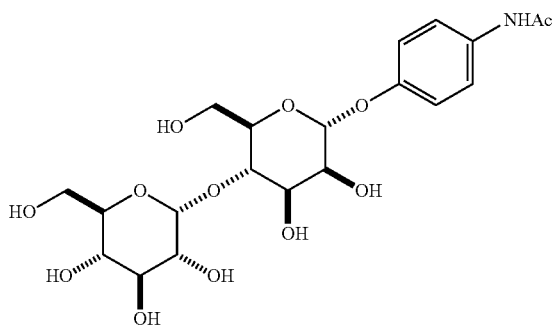

In one embodiment, the invention relates to a compound of the formula:

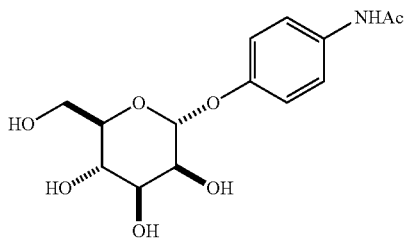 [SMILES: CC(=O)Nc1ccc(O[C@H]2O[C@H](CO)[C@@H](O)[C@H](O)[C@@H]2O)cc1]

In one embodiment, the invention relates to a compound of the formula:

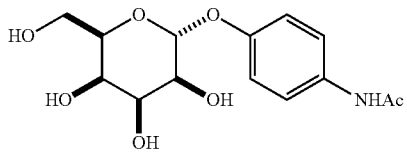

In one embodiment, the invention relates to a compound of the formula:

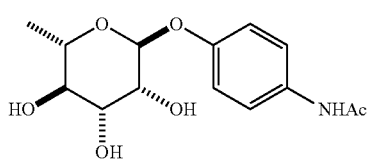 [SMILES: CC(=O)Nc1ccc(O[C@@H]2O[C@@H](C)[C@H](O)[C@@H](O)[C@H]2O)cc1]

In one embodiment, the invention relates to a compound of the formula:

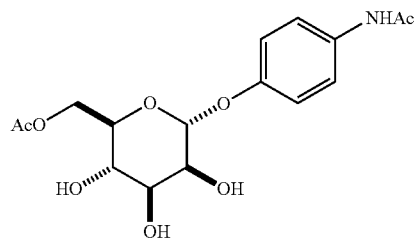 [SMILES: CC(=O)Nc1ccc(O[C@H]2O[C@H](COC(C)=O)[C@@H](O)[C@H](O)[C@@H]2O)cc1]

In one embodiment, the invention relates to a compound of the formula:

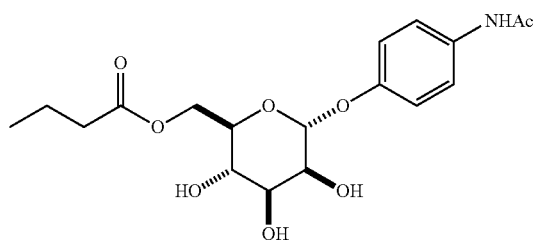

In one embodiment, the invention relates to a compound of the formula:

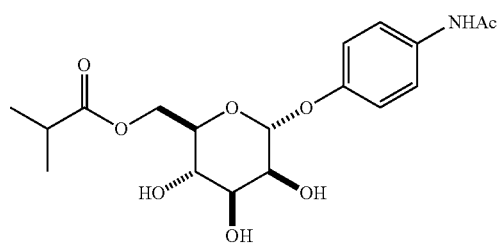 [SMILES: CC(=O)Nc1ccc(O[C@H]2O[C@H](COC(=O)C(C)C)[C@@H](O)[C@H](O)[C@@H]2O)cc1]

In one embodiment, the invention relates to a compound of the formula:

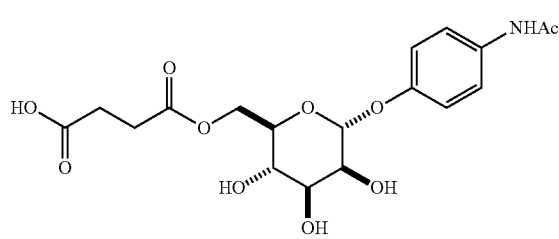

In one embodiment, the invention relates to pro-drug 2,3-dideoxy-glycoside derivatives of acetaminophen, methods for making the same, and methods of administering the same to a subject. In one embodiment, the invention relates to a compound of the formula:

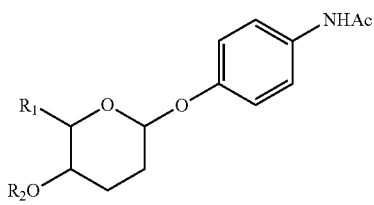

wherein $R_1$ is an alkyl, alkanediyl, aryl, aralkyl, heteroaryl, heteroaralkyl, or a substituted version of any of these groups or a protecting group, sugar, OH, or H; and $R_2$ is an alkyl, alkanediyl, aryl, aralkyl, heteroaryl, heteroaralkyl, or a substituted version of any of these groups or a protecting group, sugar, or H. In one embodiment, said compound is in combination with a pharmaceutically effective carrier.

In one embodiment, the invention relates to a compound of the formula:

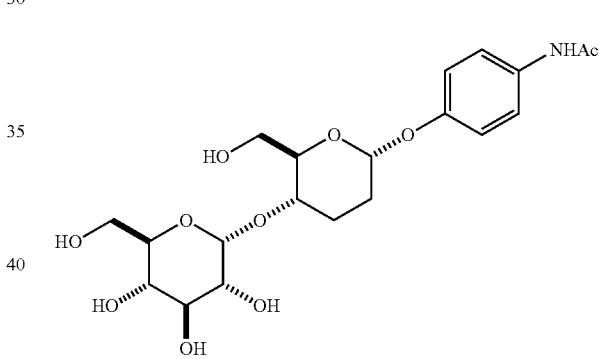

In one embodiment, the invention relates to a compound of the formula:

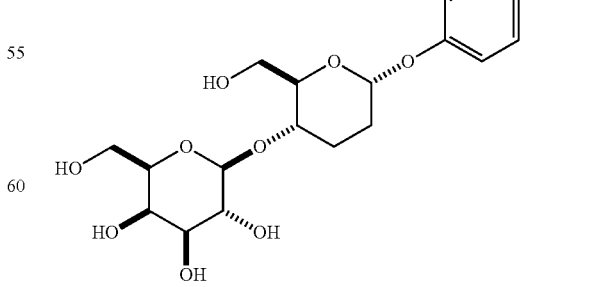

In one embodiment, the invention relates to a compound of the formula:

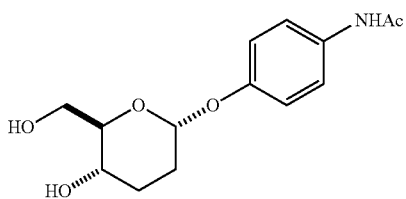 [SMILES: CC(=O)Nc1ccc(O[C@@H]2CC[C@H](O)[C@@H](CO)O2)cc1]

In one embodiment, the invention relates to a compound of the formula:

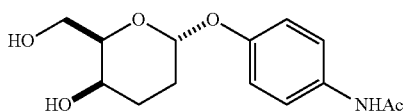 [SMILES: CC(=O)Nc1ccc(O[C@@H]2CC[C@@H](O)[C@@H](CO)O2)cc1]

In one embodiment, the invention relates to a compound of the formula:

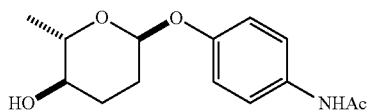 [SMILES: CC(=O)Nc1ccc(O[C@H]2CC[C@@H](O)[C@H](C)O2)cc1]

In one embodiment, the invention relates to a compound of the formula:

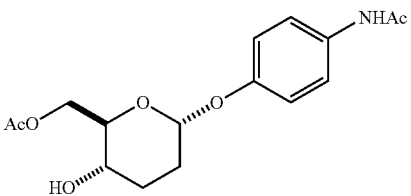 [SMILES: CC(=O)Nc1ccc(O[C@@H]2CC[C@H](O)[C@@H](COC(C)=O)O2)cc1]

In one embodiment, the invention relates to a compound of the formula:

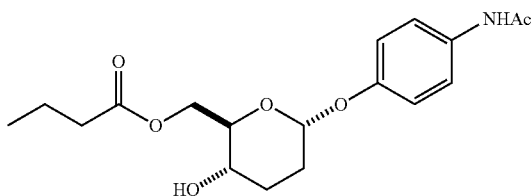 [SMILES: CCCC(=O)OC[C@H]1O[C@H](Oc2ccc(NC(C)=O)cc2)CC[C@@H]1O]

In one embodiment, the invention relates to a compound of the formula:

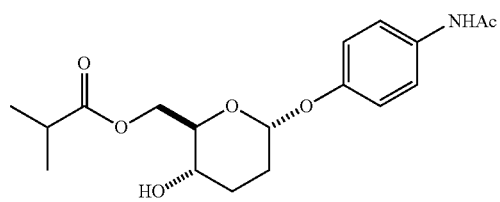 [SMILES: CC(=O)Nc1ccc(O[C@@H]2CC[C@H](O)[C@@H](COC(=O)C(C)C)O2)cc1]

In one embodiment, the invention relates to a compound of the formula:

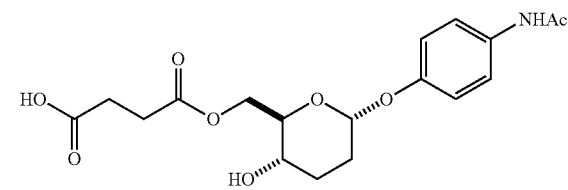 [SMILES: CC(=O)Nc1ccc(O[C@@H]2CC[C@H](O)[C@@H](COC(=O)CCC(=O)O)O2)cc1]

In one embodiment, the invention relates to a method of producing a pro-drug 2,3-hydroxy-glycoside derivative of acetaminophen, comprising: a) providing a glycoside derivative of acetaminophen wherein the glycoside has an olefin at the 2,3 position relative to the anomeric carbon bonded to the acetaminophen; b) treating said glycoside derivative of acetaminophen under conditions so as to hydroxylate the olefin and produce a 2,3-hydroxy-glycoside derivative of acetaminophen. In one embodiment, said hydroxylating conditions comprise using $OsO_4$. In one embodiment, said glycoside derivative of acetaminophen of step a) contains protecting groups. In one embodiment, said protecting groups are removed before hydroxylation of the olefin. In one embodiment, said protecting groups are removed after hydroxylation of the olefin. In one embodiment, said 2,3-hydroxy-glycoside derivative of acetaminophen derivative has the formula:

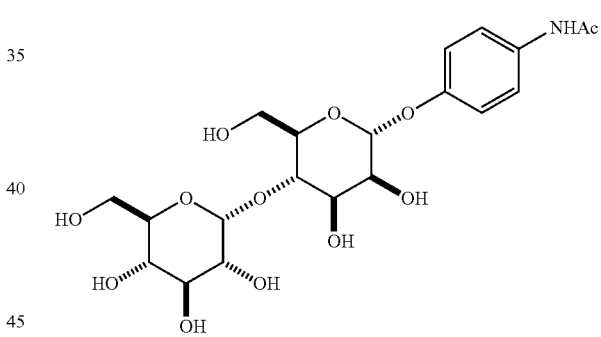

In one embodiment, said 2,3-hydroxy-glycoside derivative of acetaminophen derivative has the formula:

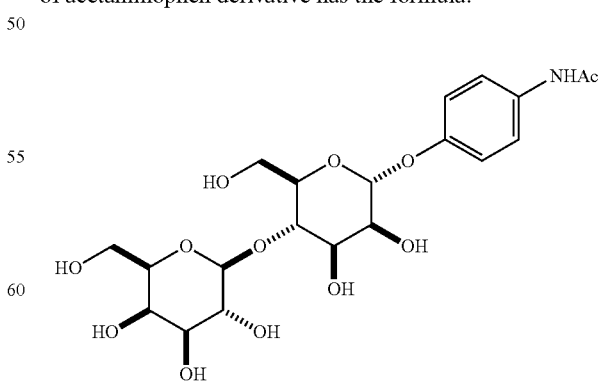

In one embodiment, said 2,3-hydroxy-glycoside derivative of acetaminophen derivative has the formula:

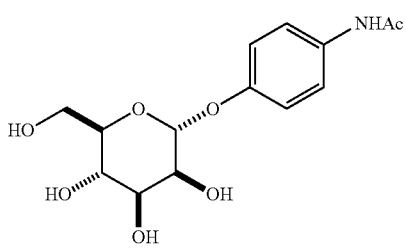

In one embodiment, said 2,3-hydroxy-glycoside derivative of acetaminophen derivative has the formula:

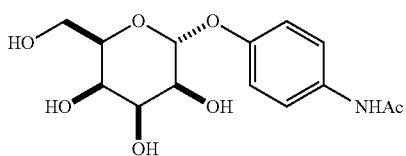

In one embodiment, said 2,3-hydroxy-glycoside derivative of acetaminophen derivative has the formula:

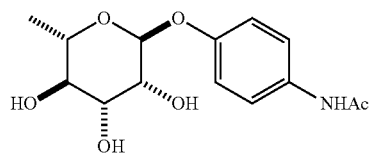

In one embodiment, said 2,3-hydroxy-glycoside derivative of acetaminophen derivative has the formula:

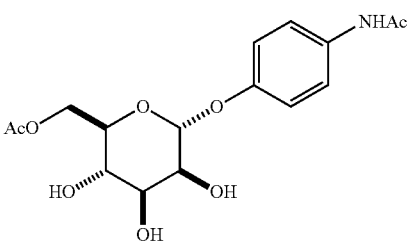

In one embodiment, said 2,3-hydroxy-glycoside derivative of acetaminophen derivative has the formula:

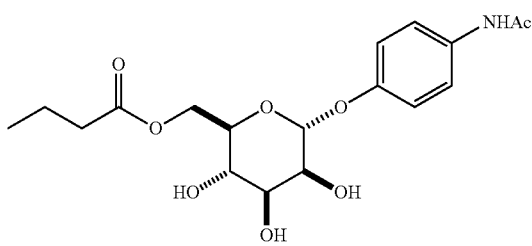

In one embodiment, said 2,3-hydroxy-glycoside derivative of acetaminophen derivative has the formula:

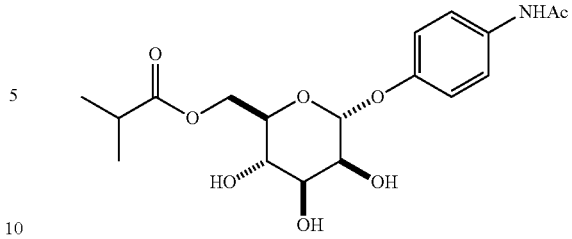

In one embodiment, said 2,3-hydroxy-glycoside derivative of acetaminophen derivative has the formula:

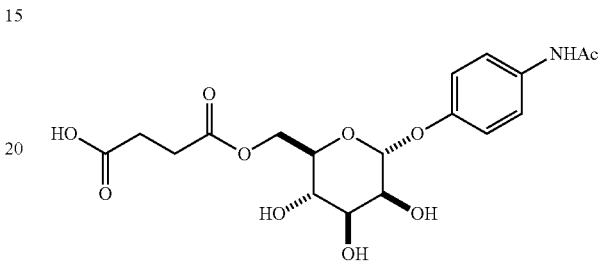

In one embodiment, the invention relates to a method of synthesizing a 2,3-dideoxy-glycoside derivative of acetaminophen wherein the glycoside has methylene groups at the 2 and 3 positions relative to the anomeric carbon bonded to the acetaminophen, comprising: a) providing a glycoside derivative of acetaminophen wherein the glycoside has an olefin at the 2,3 position relative to the anomeric carbon bonded to the acetaminophen; b) treating said glycoside derivative of acetaminophen under such reducing conditions so as to reduce the olefin and produce a 2,3-dideoxy-glycoside derivative of acetaminophen. In one embodiment, said reducing conditions comprise using TsNHNH$_2$. In one embodiment, said glycoside derivative of acetaminophen of step a) contains protecting groups. In one embodiment, said protecting groups are removed before reduction of the olefin. In one embodiment, said protecting groups are removed after reduction of the olefin. In one embodiment, said 2,3-dideoxy-glycoside derivative of acetaminophen derivative has the formula:

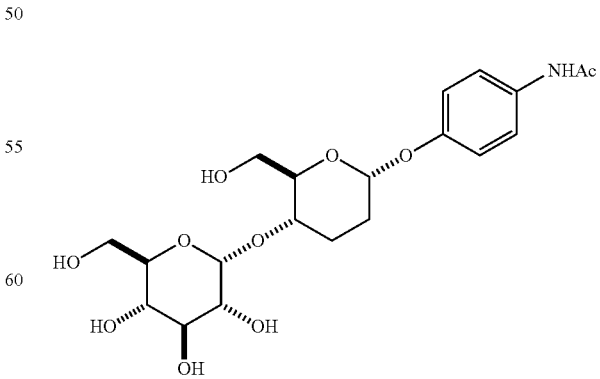

In one embodiment, 2,3-dideoxy-glycoside derivative of acetaminophen derivative has the formula:

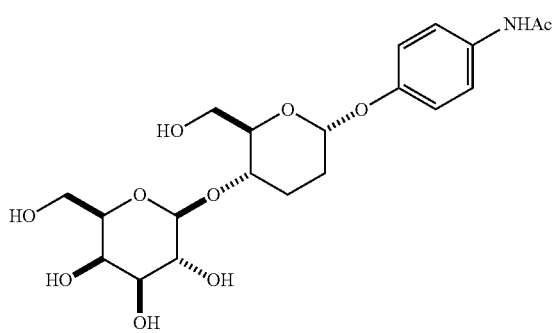

In one embodiment, said 2,3-dideoxy-glycoside derivative of acetaminophen derivative has the formula:

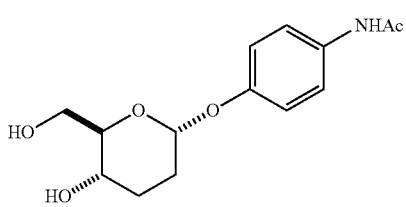

In one embodiment, said 2,3-dideoxy-glycoside derivative of acetaminophen derivative has the formula:

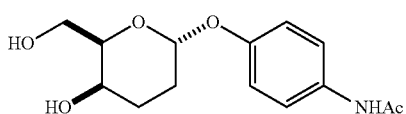

In one embodiment, said 2,3-dideoxy-glycoside derivative of acetaminophen derivative has the formula:

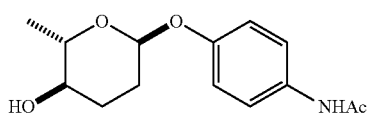

In one embodiment, said 2,3-dideoxy-glycoside derivative of acetaminophen derivative has the formula:

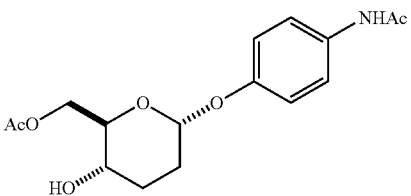

In one embodiment, said 2,3-dideoxy-glycoside derivative of acetaminophen derivative has the formula:

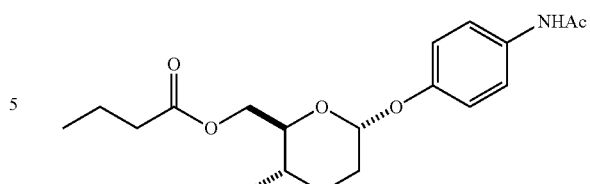

In one embodiment, said 2,3-dideoxy-glycoside derivative of acetaminophen derivative has the formula:

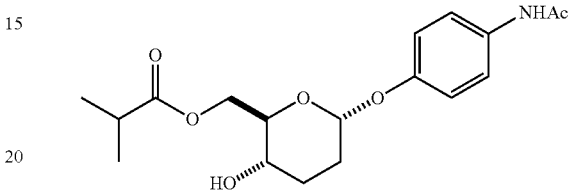

In one embodiment, said 2,3-dideoxy-glycoside derivative of acetaminophen derivative has the formula:

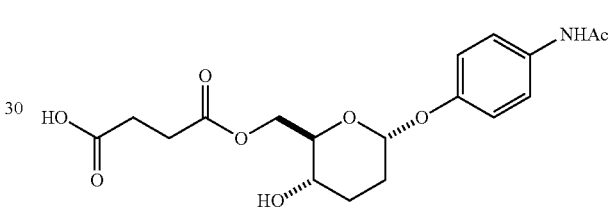

In one embodiment, the invention relates to a method of treating a subject, comprising: a) providing a subject; b) treating said subject with a 2,3-hydroxylated glycoside derivative of acetaminophen. In one embodiment, said treatment reduces pain. In one embodiment, said treatment reduces one or more symptoms of a diseased state.

In one embodiment, the invention relates to a method of treating a subject, comprising: a) providing a subject; b) treating said subject with a 2,3-dideoxy-glycoside derivative of acetaminophen. In one embodiment, said treatment reduces pain. In one embodiment, said treatment reduces one or more symptoms of a diseased state.

In one embodiment, the invention relates to a method of synthesizing a glycosylated acetaminophen, comprising: a) providing a 4-nitrophenol, a per-acylated carbohydrate, an acid catalyst, and solvent; b) glycosylating said 4-nitrophenol with said per-acylated carbohydrate with said acid catalyst in said solvent so as to produce a first product, said first product comprising a nitro group; c) treating said first product so as to reduce said nitro group to an amine and to concomitantly acylate said amine, thereby creating a second product, said second product comprising a plurality of acetate groups; d) treating said second product under conditions such that all of said acetate groups are hydrolyzed, thereby creating a third product, said third product comprising a plurality of hydroxyl groups, one of said hydroxyl groups at position C-6; and e) treating said third product under conditions such that said hydroxyl at position C-6 is selectively acylated, thereby synthesizing a glycosylated acetaminophen. In one embodiment, said per-acylated carbohydrate is pentaacetyl mannose. In one embodiment, said per-acylated carbohydrate is pentaacetyl glucsose. In one embodiment, said per-acylated carbohydrate is pentaacetyl galactose. In one embodiment, said per-acylated carbohydrate is tetraacetyl rhamnose. In one embodiment, said per-acylated carbohydrate is octaacetyl maltose. In one embodiment, said per-acylated carbohydrate is octaacetyl lactose. In one embodiment, said acid catalyst is $BF_3OEt_2$. In one embodiment, said solvent is $CH_2Cl_2$. In one embodiment, the structure of said first product is:

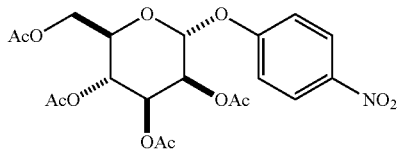 [SMILES: CC(=O)OC[C@H]1O[C@H](Oc2ccc([N+](=O)[O-])cc2)[C@@H](OC(C)=O)[C@@H](OC(C)=O)[C@@H]1OC(C)=O]

In one embodiment, the structure of said second product is:

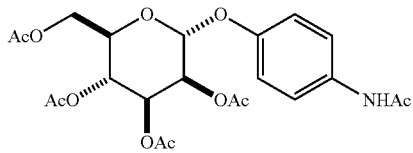 [SMILES: CC(=O)Nc1ccc(O[C@H]2O[C@H](COC(C)=O)[C@@H](OC(C)=O)[C@H](OC(C)=O)[C@@H]2OC(C)=O)cc1]

In one embodiment, the structure of said third product is:

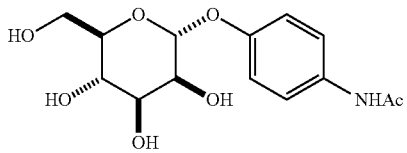 [SMILES: CC(=O)Nc1ccc(O[C@H]2O[C@H](CO)[C@@H](O)[C@H](O)[C@@H]2O)cc1]

In one embodiment, the structure of said glycosylated acetaminophen is:

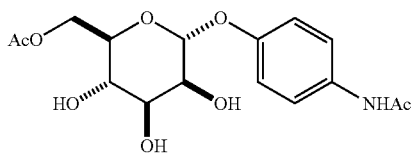 [SMILES: CC(=O)Nc1ccc(O[C@H]2O[C@H](COC(C)=O)[C@@H](O)[C@H](O)[C@@H]2O)cc1]

In one embodiment, the invention relates to a method of synthesizing an amino hydroxyl glycosylated acetaminophen analog, comprising: a) providing acetylated protecting group protected 2,3-olefin glycosylated acetaminophen analog, m-CPBA, and solvent; b) epoxidizing said acetylated protecting group protected 2,3-olefin glycosylated acetaminophen analog with said m-CPBA in said solvent so as to produce a first product, said first product comprising an 2,3-epoxide group; c) treating said first product so as to change said epoxide group to an azide and hydroxyl group, thereby creating a second product, said second product comprising an azide and hydroxyl group; d) treating said second product under conditions such that all of said azide groups are hydrogenated and reduced, thereby creating a third product, said third product comprising an amine and hydroxyl groups; and e) treating said third product under conditions such that said acetylated hydroxyl protecting groups are selectively removed, thereby synthesizing an amino hydroxyl glycosylated acetaminophen analog. In one embodiment, the structure of said first product is:

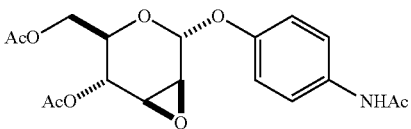

In one embodiment, the structure of said second product is selected from the group:

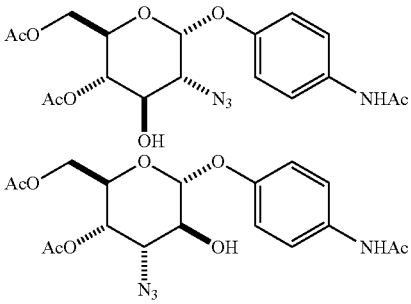

In one embodiment, the structure of said third product is selected from the group:

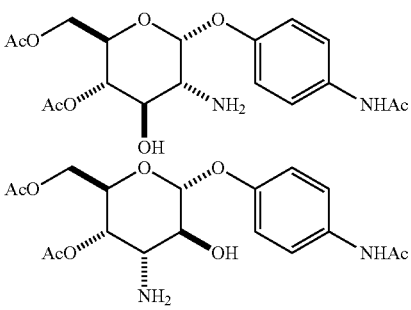

In one embodiment, the structure of said amino hydroxyl glycosylated acetaminophen analog is selected from the group:

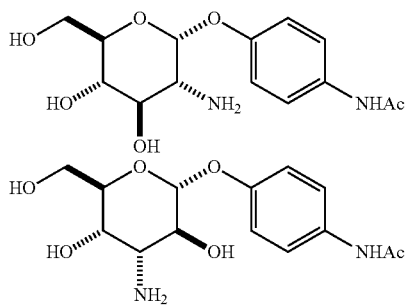

In one embodiment, the invention relates to a method of synthesizing 2,3-dideoxy-glycoside derivative of acetaminophen, comprising: a) providing protecting group protected 2,3-olefin glycosylated acetaminophen analog, $H_2$, and a metal which catalyzes hydrogenation; b) hydrogenating said protecting group protected 2,3-olefin glycosylated acetaminophen analog with said $H_2$ and metal so as to produce a first product, said first product comprising a protecting group protected 2,3-dideoxy-glycoside derivative of acetaminophen; c) treating said first product so as to remove the protecting group of said first product, thereby creating a 2,3-dideoxy-glycoside derivative of acetaminophen. In one embodiment, the structure of said protecting group protected 2,3-olefin glycosylated acetaminophen analog is selected from the group:

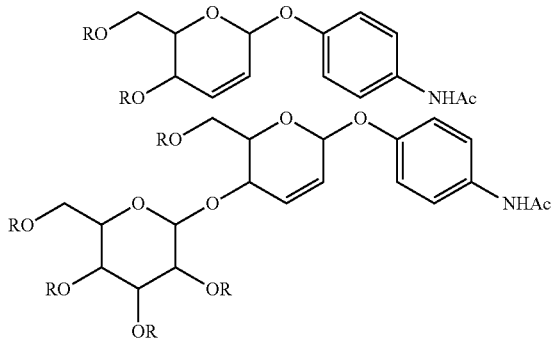

wherein R is a protecting group, acetate, or H.

In one embodiment, the structure of said first product is selected from the group:

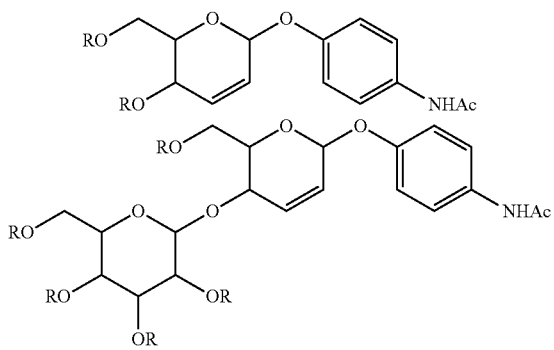

wherein R is a protecting group, acetate, or H.

In one embodiment, the structure of said 2,3-dideoxy-glycoside derivative of acetaminophen is selected from the group:

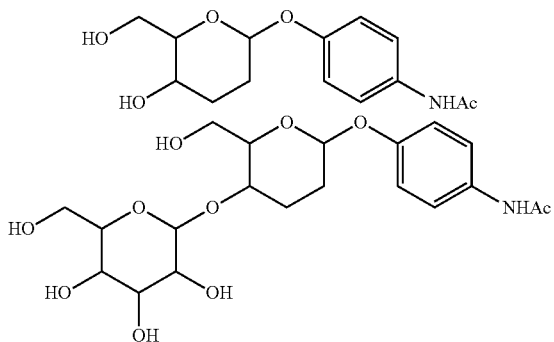

In one embodiment, said metal which catalyzes hydrogenation is selected from the group: nickel, platinum, palladium, rhodium, and ruthenium based metals.

DETAILED DESCRIPTION OF THE INVENTION

U.S. Pat. No. 5,693,767, hereby incorporated by reference [1], describes the preparation of glycosylated acetaminophen analogs with an olefin at the 2,3 position in the carbohydrate. Specifically, the glucal 1, maltal 2 and lactal 3 analogs were prepared and claimed (FIG. 1). The presence of the olefin at C2-C3 is known to have a detrimental effect on the stability of the glycosidic linkage (Stache, et al.) [2], particularly in mildly acidic solutions.

It is desired to have stable formulations of these acetaminophen analogs. Thus, described herein is a series of new analogs created by modifying the olefin and tested both for their stability and pharmacokinetic profile. Regarding the added benefits of glycosylated analogs versus acetaminophen, acetaminophen has two other problems in addition to its poor solubility. Over a period of time in solution, acetaminophen is prone to both de-acylation as well as oxidation (FIG. 2). In order to minimize de-acylation, the formulation for acetaminophen is buffered at pH 6. To prevent oxidation, an anti-oxidant (in this case, cysteine) is added to the formulation [3]. The products of both processes (4-aminophenol and N-acetyl-p-benzoquinone imine, respectively) are toxic, with the 4-amidophenol more associated with the known toxicity of acetaminophen [4].

While not intending to limit the invention in any way to a mechanism, it is believed that, with the presence of the carbohydrate attached at the phenol, the problem of oxidation may be minimized (FIG. 2), since the electronics of the ring system (due to the phenol converted to a phenyl ether), and hence the N-acyl group, are changed (and therefore the rate of hydrolysis of the N-acyl group is also changed) (FIG. 2).

In one embodiment, the invention comprises new analogs that have the olefin oxidized to a diol, and reduced, in order to make the acetaminophen analogs more stable in slightly acidic solutions for a longer period of time. Two direct ways to remove the olefin, while minimizing the regio- and stereochemical issues, would be by either hydrogenating it or by cis hydroxylation. As compared to the analog with the olefin, the cis-hydroxylated and hydrogenated analogs should both have approximately the same stability towards acidic formulations, but greater than that with the olefin (FIG. 3).

Additionally, of the three analogs, the analogs with the olefin and hydrogenated olefin are expected to have roughly the same water-solubility, and the analog with the olefin converted to the diol should have better water-solubility (FIG. 4). Thus, given these two criteria (stability towards acidic formulations, and water-solubility), the one with the diol at the 2,3-position should be most desirable.

In the case of the glycosylation with disaccharides, as shown in FIG. 4, the analog with the olefin oxidized to the diol has 7 hydroxyls rather than 5 like the other two. This will increase the water solubility of the compound. Indeed, in the case for the monosaccharides, the difference is quite significant. This process doubled the number of hydroxyls in the molecule that would be available for hydrogen bonding in water, and hence better water solubility. The water solubility is such that we are able to obtain NMR spectra of this compound in $D_2O$. It should be noted that, unlike the analogs patented previously, we have now been able to isolate the α anomer in pure form and hence the difference in the anomeric bonds of the two analogs in FIG. 5.

Preparation of the Analogs

The present invention contemplates a variety of synthesis schemes. In one embodiment, acetaminophen derivative A, hydroxylation could be performed first (yielding B), followed by removal of the protecting groups (yielding C); in another embodiment, the protecting groups could be removed (yielding D), followed by hydroxylation of the olefin (yielding C). The preference here is for initial cis-hydroxylation, since hydroxylating agents, such as OsO$_4$ are highly toxic and is preferred not to have it in the last step of a synthesis.

In another embodiment, the invention describes the method presented in FIG. 6A for the synthesis of a 2,3-dihydroxy glycoside acetaminophen derivative:

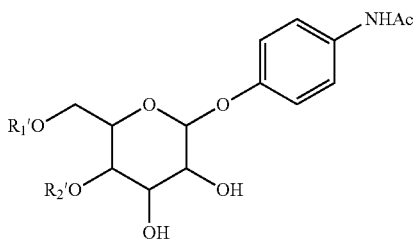

wherein R$_1$' is an alkyl, alkanediyl, alkynyl, acyl, aryl, arenediyl, aralkyl, heteroaryl, heteroarenediyl, heteroaralkyl, or a substituted version of any of these groups or a protecting group, phosphate, sulfonate, or H; and R$_2$' is an alkyl, alkanediyl, alkynyl, acyl, aryl, arenediyl, aralkyl, heteroaryl, heteroarenediyl, heteroaralkyl, methyl, allyl, cyclopropyl, carbinol, n-propargyl or a substituted version of any of these groups or a protecting group, H, phosphate, sulfonate, or sugar group.

In another embodiment, the method starts with disaccharide 1 (described and claimed in the 1997 patent) [1], and cis-hydroxylation, could be performed first, followed by hydrolysis of the protective groups; or the protective groups could be removed, followed by cis-hydroxylation of the olefin. FIG. 6B outlines one embodiment of the method for the first preparation of the new analogs. In another embodiment, the present invention contemplates a method starting with the maltal analog 2 (described and claimed in the 1997 patent) [1], and cis-hydroxylation could be performed first, followed by hydrolysis of the protective acetates; or alternatively the acetates could be removed, followed by cis-hydroxylation of the olefin. Once again, the preference here is for initial cis-hydroxylation, since OsO$_4$ is highly toxic and is best not to have it in the last step of a synthesis.

In another embodiment, the present invention contemplates a method starting with the monosaccharide derivative 5. This is described in FIG. 6C. Surprisingly, cis-hydroxylation with OsO$_4$ of the di-acetate shown in FIG. 6C failed to provide any useable material. Thus, the case of the monosaccharide is more restrictive (FIG. 6C). While not intending to be limited by any particular mechanism, it is believed that this is due to a little-known phenomenon of OsO$_4$ oxidations of allylic acetates in which the acetate participates in the intermediate and leads to a complex mixture of products. As a result, the present invention contemplates an embodiment of the method wherein the removal of the acetates precedes the cis-hydroxylation, with OsO$_4$ being employed in the last step.

It may be possible to employ chloroacetates in one embodiment as the protecting group in the above sequence, thus reducing the participation of the protecting group and allowing for oxidation before removal of the acetates. Or it may be that polymer-bound OsO$_4$ (OsEnCat) may be employed in another embodiment, limiting the amount of Os contamination of the product. Or perhaps another, entirely different oxidant may be effective in yet another embodiment of the method.

The present invention also contemplates embodiments wherein the olefin can be reduced to make the two 2,3 dideoxyanalogs shown in FIG. 7A and FIG. 7B. It does not matter much whether reduction precedes hydrolysis of the acetates or vice-versa, so the present invention contemplates both synthetic approaches.

In another embodiment, the present invention contemplates a 2,3-dideoxy-glycoside acetaminophen derivative and methods for making the same. Below is one embodiment of an initial sequence of steps undertaken for the preparation the reduced versions of the analogs.

In one embodiment, the invention considers the synthesis of a 2,3-dideoxy-glycoside acetaminophen derivative F, starting from a protected 2,3-dideoxy-glycoside derivative of acetaminophen A. In one embodiment, the synthesis method comprises the reduction of the olefin (yielding E) followed by removal of the protecting groups (yielding F). In an alternative embodiment, the synthesis method comprises producing a 2,3-dideoxy-glycoside acetaminophen derivative F, by starting from a protected 2,3-dideoxy-glycoside derivative of acetaminophen A. In one embodiment, the synthesis method comprises the removal of the protecting groups (yielding G) followed by the reduction of the olefin (yielding F).

In another embodiment, the invention contemplates the method presented in FIG. 7A for the synthesis of a 2,3-dideoxy-glycoside acetaminophen derivative:

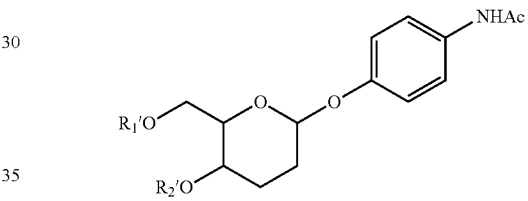

wherein R$_1$' is an alkyl, alkanediyl, alkynyl, acyl, aryl, arenediyl, aralkyl, heteroaryl, heteroarenediyl, heteroaralkyl, or a substituted version of any of these groups or a protecting group, phosphate, sulfonate, or H; and R$_2$' is an alkyl, alkanediyl, alkynyl, acyl, aryl, arenediyl, aralkyl, heteroaryl, heteroarenediyl, heteroaralkyl, methyl, allyl, cyclopropyl, carbinol, n-propargyl or a substituted version of any of these groups or a protecting group, H, phosphate, sulfonate, or sugar group.

It is not intended that the present invention be limited to a single synthesis approach. In one embodiment, the method comprises reduction (in this case using toluene sulfonylhydrazine) followed by removal of the protecting group acetates. In another embodiment, the method comprises removal of the acetates followed by reduction (this works equally well). The reduction sequence proceeds well for the disaccharide case, as shown in FIG. 7B.

Based on initial pharmacokinetic data, we decided to make a few more analogs modified at C-6 (to be discussed in the pK section). The acetate was prepared in two different manners; either by selective hydrolysis of the diacate 6, or by selective acylation of the diol 1 to form 6-acetate 14, followed by cis hydroxylation of the olefin to the 6-acetyl mannose analog 15 (FIG. 8). Note that the hydrolysis of the diacetate provided the unexpected 6-acetate 14 (FIG. 8). While not intending to be limited to any particular mechanism, this may be the result of initial hydrolysis of the 6-acetate followed by acyl migration of the 4-acetate to C-6.

We also prepared the 6-butyryl, 6-isobutyryl and 6-hemisuccinate (R=HO$_2$CCH$_2$CH$_2$CO—) in a similar manner as above starting with diol 1. Although there is some precedent for acylating the mannose tetra-ol 8 at the C-6 selectively, we found it was much simpler to acylate the diol 1 and then cis-hydroxylate the olefin. Thus, the latter approach is a preferred embodiment.

Again, while not intending to be limited any particular analog, the analog that seems to have some of the best characteristics is compound 15, the 6-acetylmannose acetaminophen analog. This seems to have the best combination of water solubility, quick release of the acetaminophen, and AUC (area under the curve).

Finally, we also wanted to prepare the 6-deoxymannose analog of acetaminophen, and this was accomplished by selectively tosylating the primary hydroxyl of diol 1, followed borohydride reduction and cis hydroxylation of the olefin. It should be noted that, although the C-6 tosylate of mannose analog 8 can easily be made, only the bicyclic compound shown in FIG. 10 was isolated. Again, while not intending to be limited to any mechanism, this may be due to intramolecular displacement of the tosylate by the C-2 hydroxyl.

BRIEF DESCRIPTION OF THE FIGURES

For a more complete understanding of the features and advantages of the present invention, reference is now made to the detailed description of the invention along with the accompanying figures. So there is no confusion, the two different numbering conventions that are being used for the carbohydrate are here clarified. When the text refers to a "2,3-dideoxy-glycoside derivative" the numbering begins at the anomeric carbon (C-1) and corresponds to the numbering in FIG. 3 and FIG. 4. However, for the formal naming of the compounds in these 2 paragraphs, the numbering corresponds to the numbering of the pyran ring system where the numbering begins at the oxygen atom (below).

U.S. Pat. No. 5,693,767 [1] was found to be susceptible to glycoside hydrolyzation. Many of the compounds considered in the current application are monosaccharide analogs; the lead compound is a monosaccharide analog. However.

FIG. 4 illustrates the improvement of the current analogs over those patented before are of the disaccharide variety. Nonetheless, the present invention should in no way be limited to disaccharide analogs.

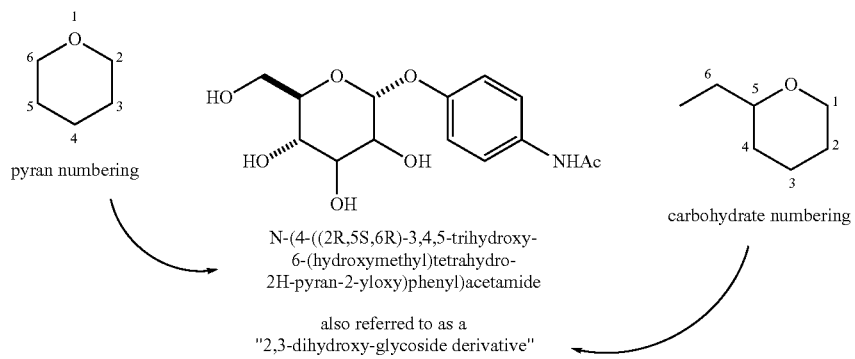

Figure 1:
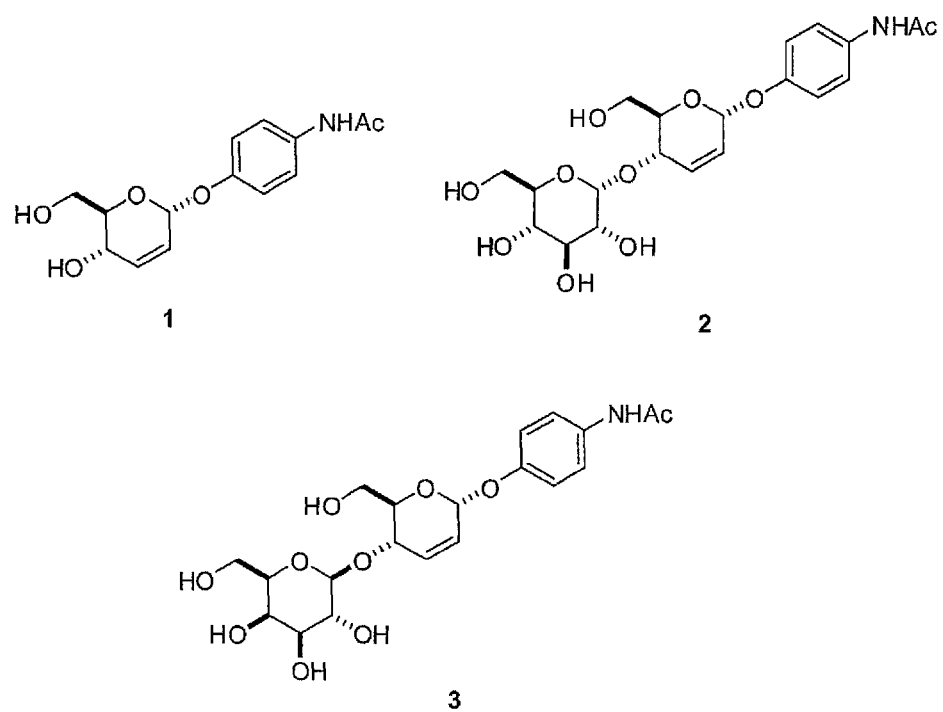

FIG. 1 shows the glycosylated acetaminophen analogs with an olefin at the 2,3 position in the carbohydrate. Specifically, the glucal 1, maltal 2 and lactal 3 analogs were prepared and claimed in the patent from 1997 (U.S. Pat. No. 5,693,767) [1].

Figure 2:
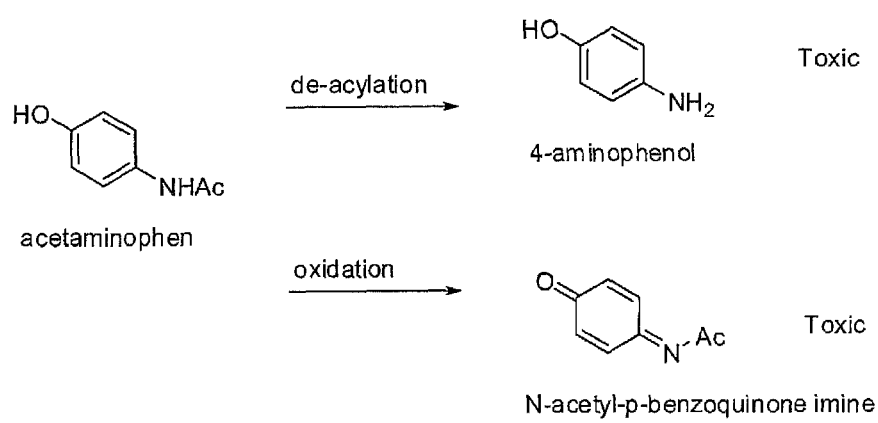
Figure 2:
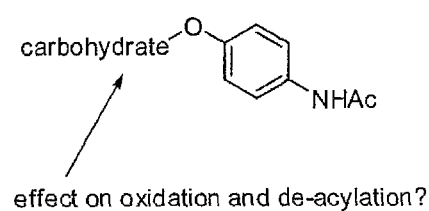

FIG. 2 shows how acetaminophen is prone to both de-acylation (to 4-aminophenol) as well as oxidation (N-acetyl-p-benzoquinone imine) forming toxic biproducts. An acetaminophen carbohydrate derivative may reduce the formation of toxic biproducts associated with acetaminophen.

Figure 3:
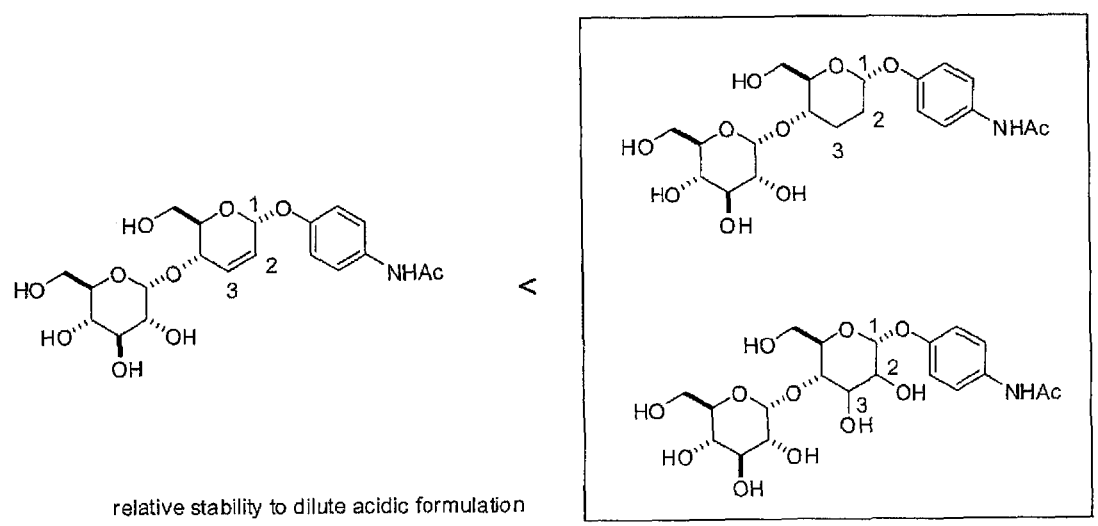
FIG. 3 illustrates the improvement of the current analogs over those patented before are of the disaccharide variety. The improvement of the pro-drug analogs contemplated by this invention, however, should in no way be limited to disaccharides.
Figure 4:
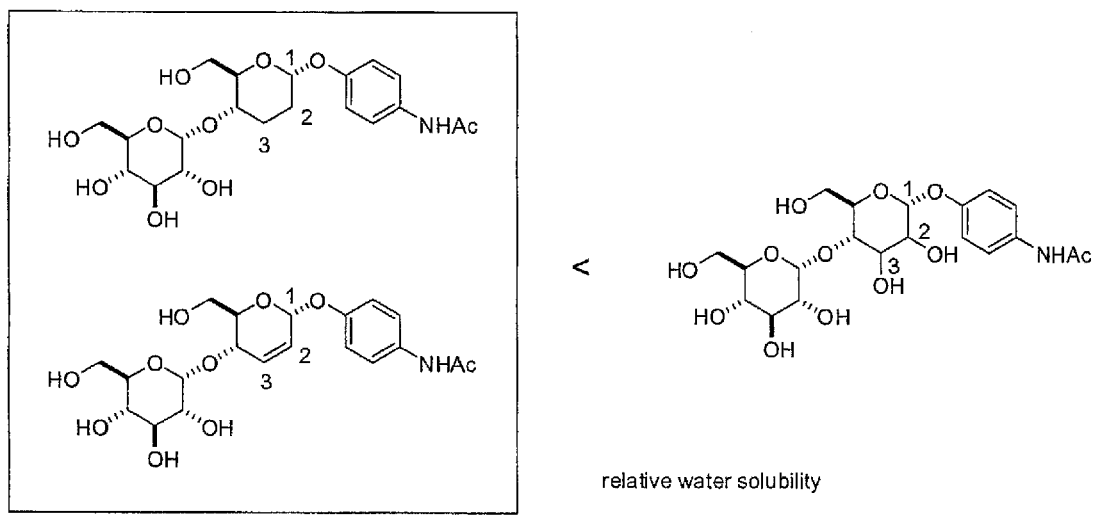
FIG. 4 illustrates the greater solubility of a 2,3-dihydroxy-glycoside derivative of acetaminophen (N-(4-((2R,5S,6R)-3,4-dihydroxy-6-(hydroxymethyl)-5-(2R,3R,4S,5S,6R)-3,4,5-trihydroxy-6-(hydroxymethyl)tetrahydro-2H-pyran-2-yloxy)tetrahydro-2H-pyran-2-yloxy)phenyl)acetamide) versus the both a 2,3-dideoxy-glycoside derivative of acetaminophen (containing an olefin at the 2,3 glycoside position) (N-(4-((2R,5S,6R)-6-(hydroxymethyl)-5-((2S,3R,4S,5S,6R)-3,4,5-trihydroxy-6-(hydroxymethyl)tetrahydro-2H-pyran-2-yloxy)-5,6-dihydro-2H-pyran-2-yloxy)phenyl)acetamide) or 2,3-dideoxy-glycoside derivative of acetaminophen (N-(4-((2R,5S,6R)-6-(hydroxymethyl)-5-((2S,3R,4S,5S,6R)-3,4,5-trihydroxy-6-(hydroxymethyl)tetrahydro-2H-pyran-2-yloxy)tetrahydro-2H-pyran-2-yloxy)phenyl)acetamide). While many of the compounds considered in the current application are on the monosaccharide analogs.
Figure 5:
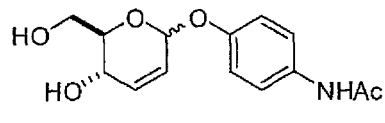
FIG. 5 illustrates the greater solubility of a 2,3-dihydroxy-glycoside derivative of acetaminophen (N-(4-((2R,3S,4S,5S,6R)-3,4,5-trihydroxy-6-(hydroxymethyl)tetrahydro-2H-pyran-2-yloxy)phenyl)acetamide) versus the 2,3-dideoxy-glycoside derivative of acetaminophen (N-(4-((5S,6R)-5-hydroxy-6-(hydroxymethyl)-5,6-dihydro-2H-pyran-2-yloxy)-phenyl)acetamide) found in the U.S. Pat. No. 5,693,767 [1].
Figure 5:
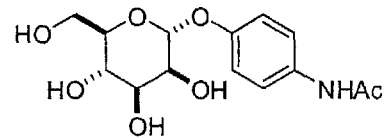
Figure 6A:
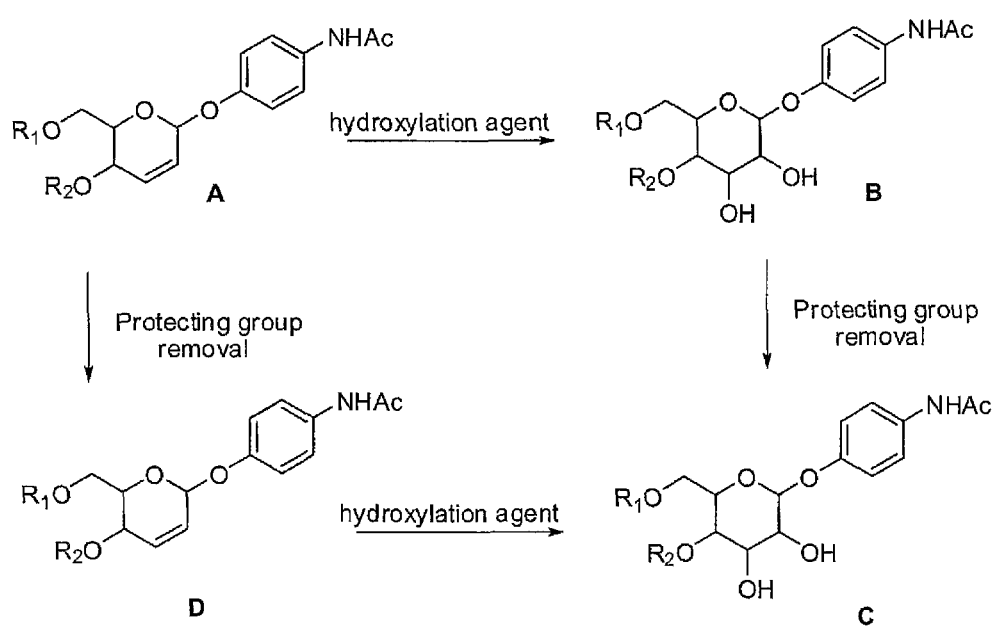

FIG. 3 illustrates the greater stability of two compounds considered in the current invention compared to a compound found in U.S. Pat. No. 5,693,767 [1]. The compound from FIG. 6A is generic schematic of one embodiment of the present invention for the synthesis of a 2,3 hydroxylated glycoside derivative of acetaminophen C.

Figure 6B:
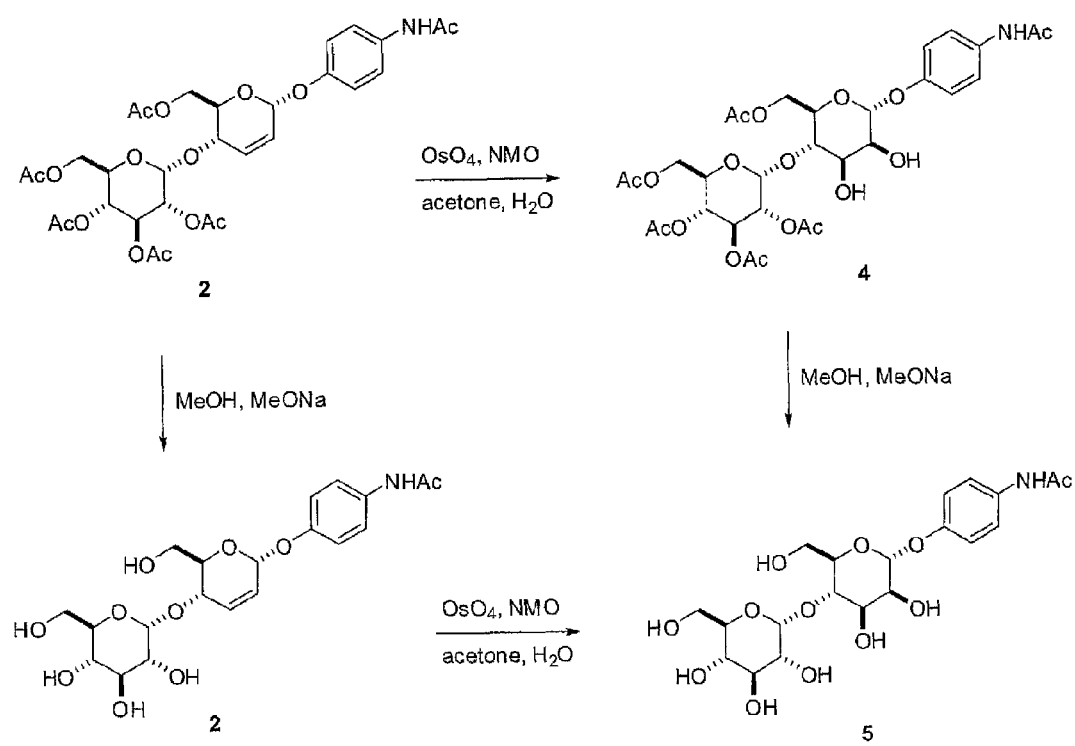

FIG. 6B is a specific schematic of one embodiment of the present invention for the synthesis of a 2,3 cis-hydroxylated glycoside derivative of acetaminophen 3 (N-(4-((2R,3S,4R,5S,6R)-3,4-dihydroxy-6-(hydroxymethyl)-5-((2R,3R,4S,5S,6R)-3,4,5-trihydroxy-6-(hydroxymethyl)tetrahydro-2H-pyran-2-yloxy)tetrahydro-2H-pyran-2-yloxy)phenyl)acetamide).

Figure 6C:
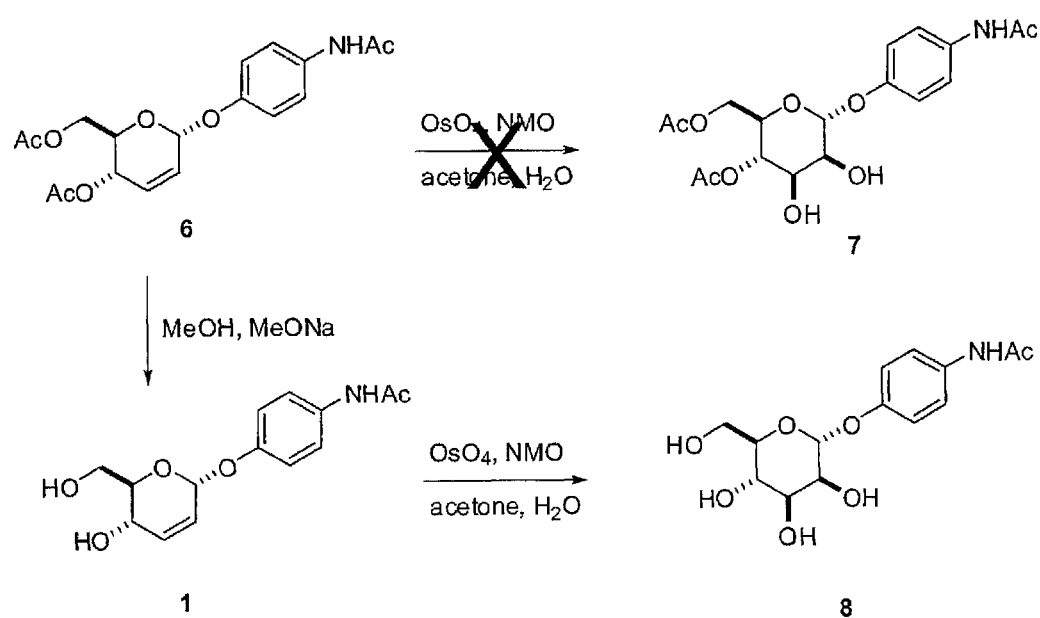

FIG. 6C is another specific schematic of one embodiment of the present invention for the synthesis of a 2,3 cis-hydroxylated glycoside derivative of acetaminophen 8 (N-(4-((2R,3S, 4S,5S,6R)-3,4,5-trihydroxy-6-(hydroxymethyl)tetrahydro-2H-pyran-2-yloxy)phenyl)acetamide).

Figure 7A:
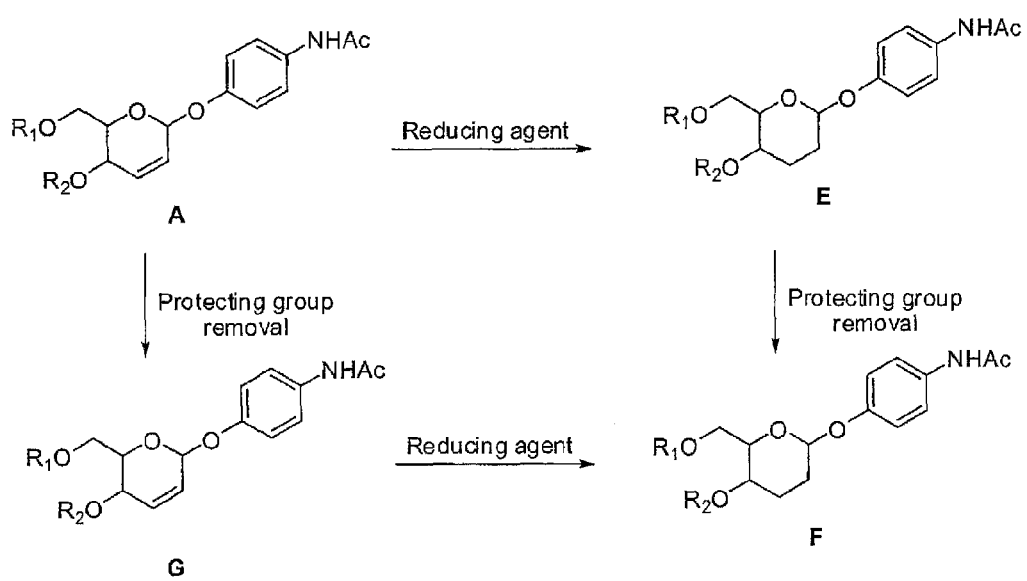

FIG. 7A is generic schematic of one embodiment of the present invention for the synthesis of a 2,3-dideoxy-glycoside derivative of acetaminophen F.

Figure 7B:
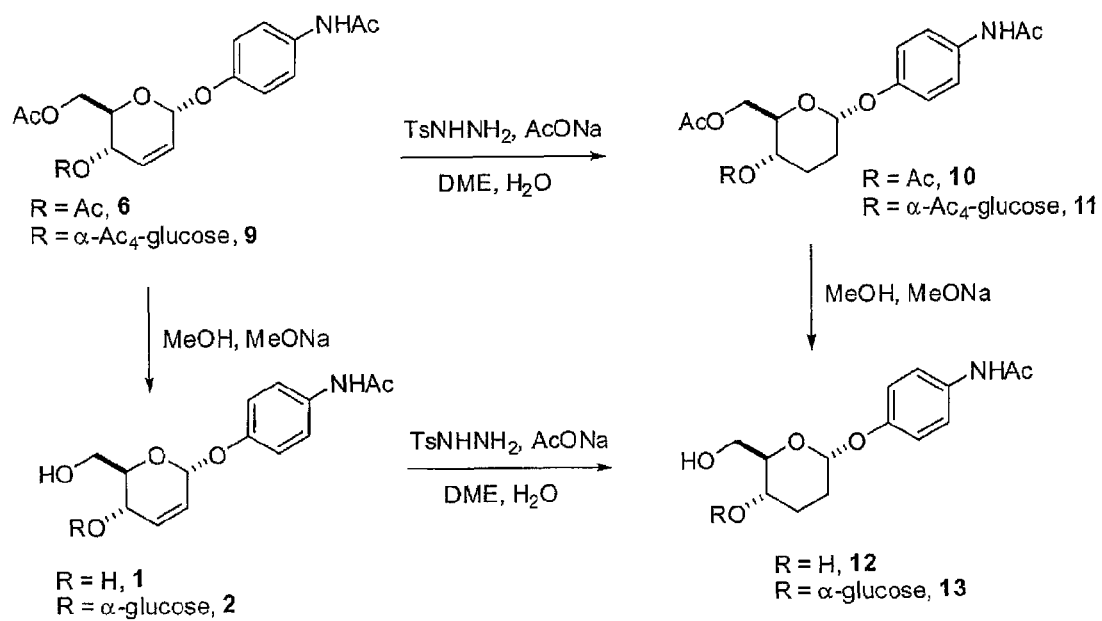

FIG. 7B is a specific schematic of one embodiment of the present invention for the synthesis of a 2,3-dideoxy-glycoside derivative of acetaminophen 10 (N-(4-((2R,5S,6R)-5-hydroxy-6-(hydroxymethyl)tetrahydro-2H-pyran-2-yloxy)phenyl)acetamide).

Figure 7C:
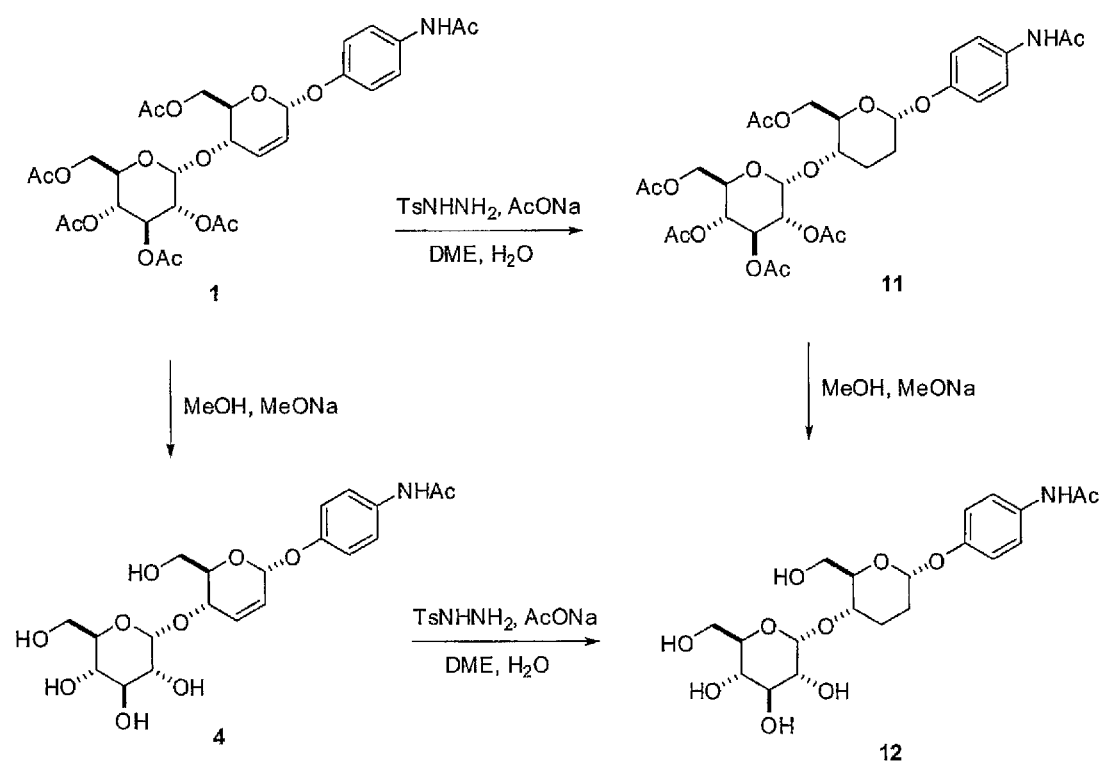

FIG. 7C is a specific schematic of another embodiment of the present invention for the synthesis of a 2,3-dideoxy-glycoside derivative of acetaminophen 12 (N-(4-((2R,5S,6R)-6-(hydroxymethyl)-5-((2S,3R,4S,5S,6R)-3,4,5-trihydroxy-6-(hydroxymethyl)tetrahydro-2H-pyran-2-yloxy)tetrahydro-2H-pyran-2-yloxy)phenyl)acetamide).

Figure 8:
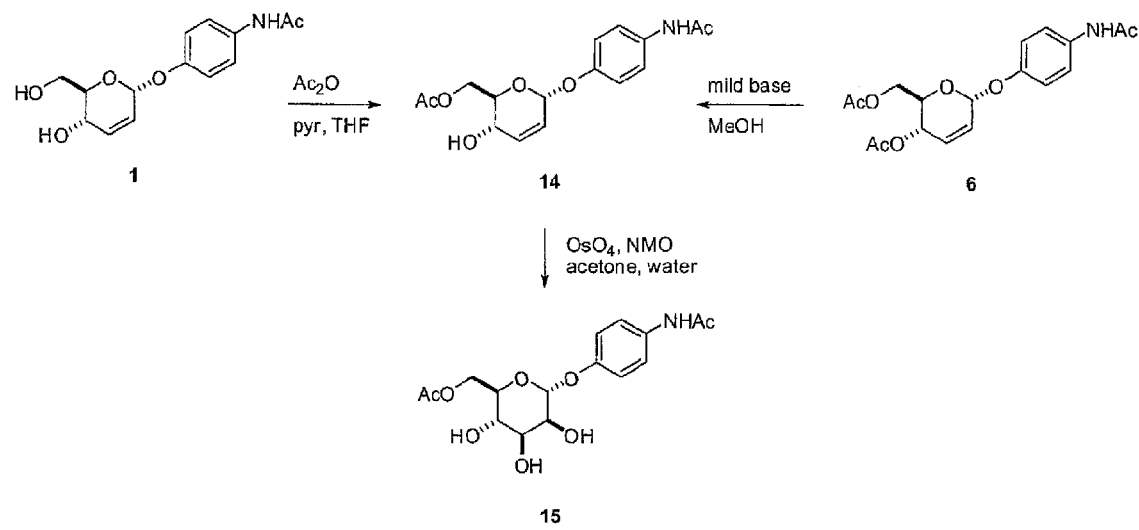

FIG. 8 shows a specific schematic of another embodiment of the present invention for the synthesis of the acetate 14 prepared in two different manners; either by selective hydrolysis of the diacate 6, or by selective acylation of the diol 1 to form 6-acetate 14, followed by cis hydroxylation of the olefin to the 6-acetyl mannose analog 15.

Figure 9:
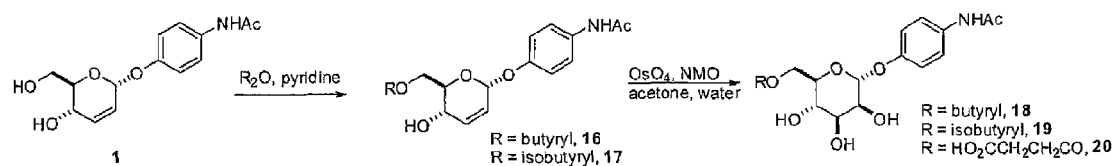

FIG. 9 shows a specific schematic of another embodiment of the present invention for the synthesis of 6-butyryl, 6-isobutyryl and 6-hemisuccinate (R=HO$_2$CCH$_2$CH$_2$CO—) analogs.

Figure 10:
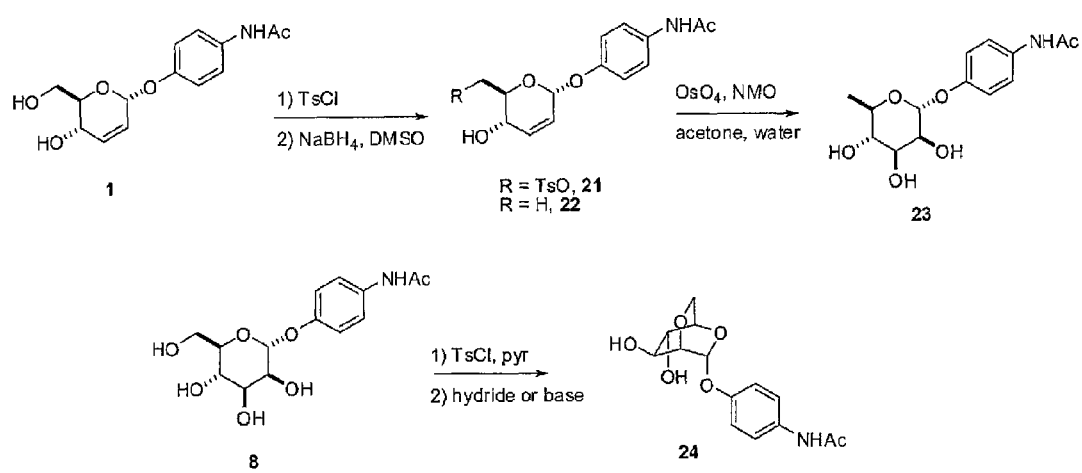

FIG. 10 shows a specific schematic of another embodiment of the present invention for the synthesis of the 6-deoxymannose analog of acetaminophen.

Figure 11:
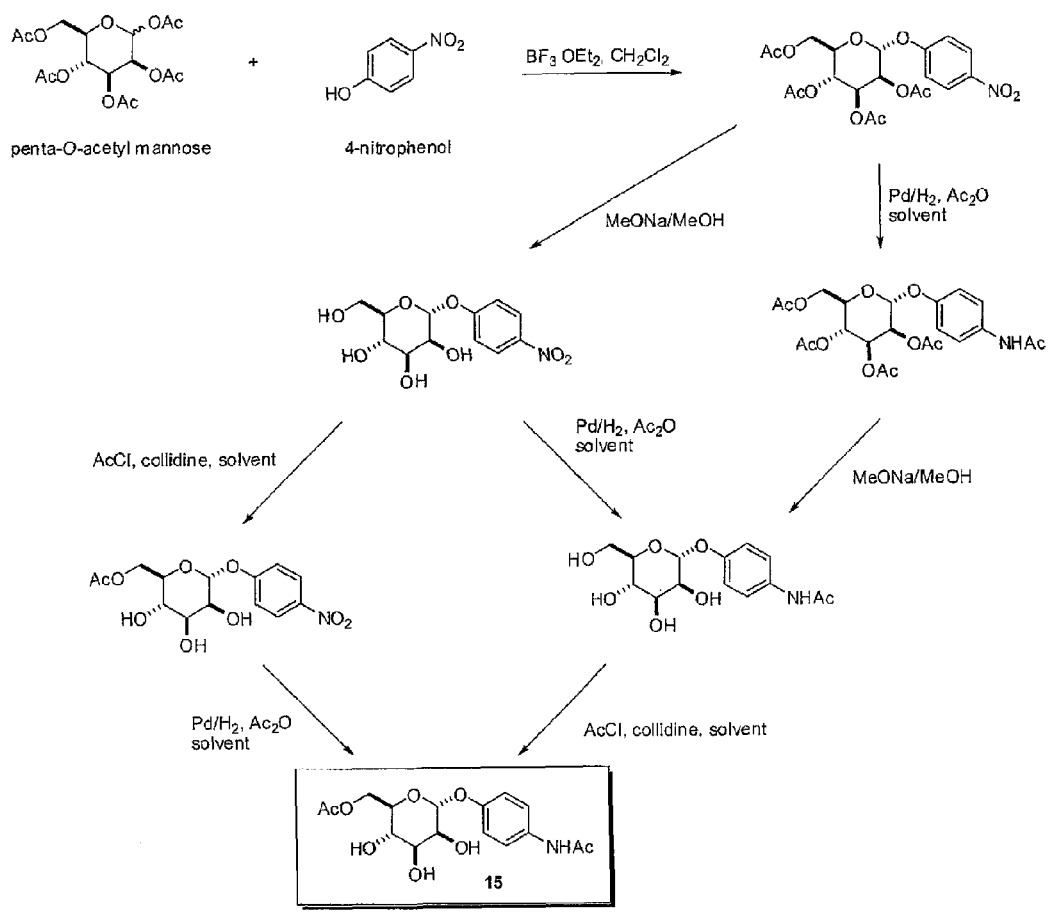

FIG. 11 shows a specific schematic of another embodiment of the present invention for the synthesis of compound 15.

Figure 12:
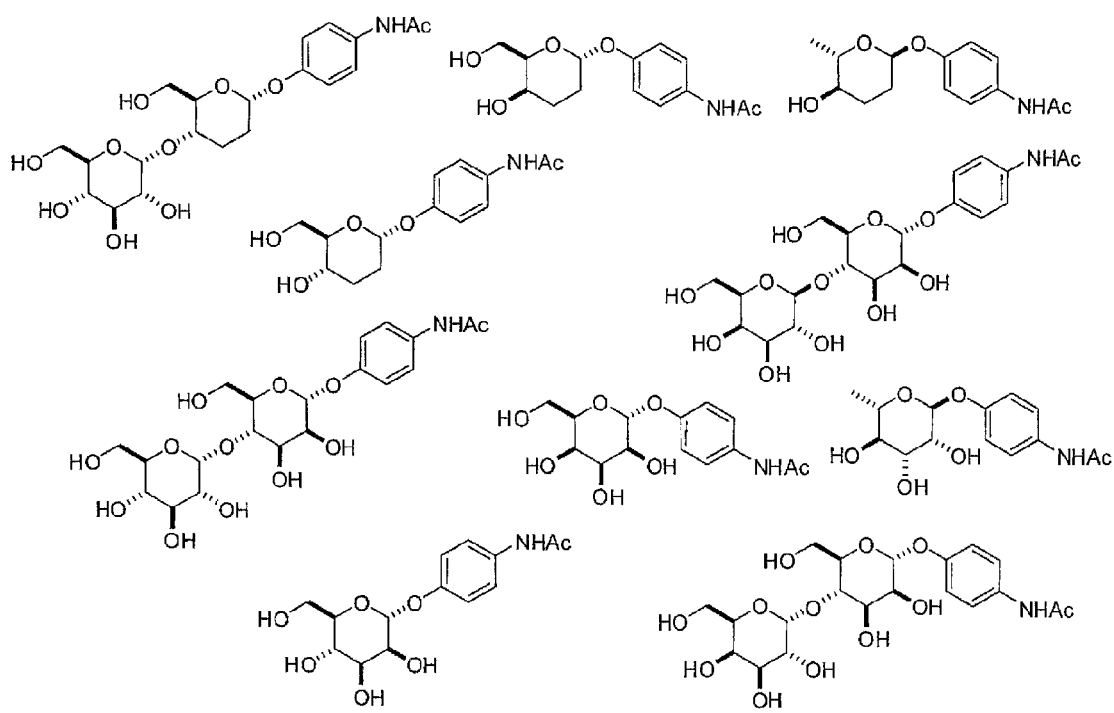

FIG. 12 is another embodiment of the present invention. These are non-limiting examples of both 2,3 hydroxylated and 2,3-dideoxy-glycoside derivatives of acetaminophen.

Figure 13:
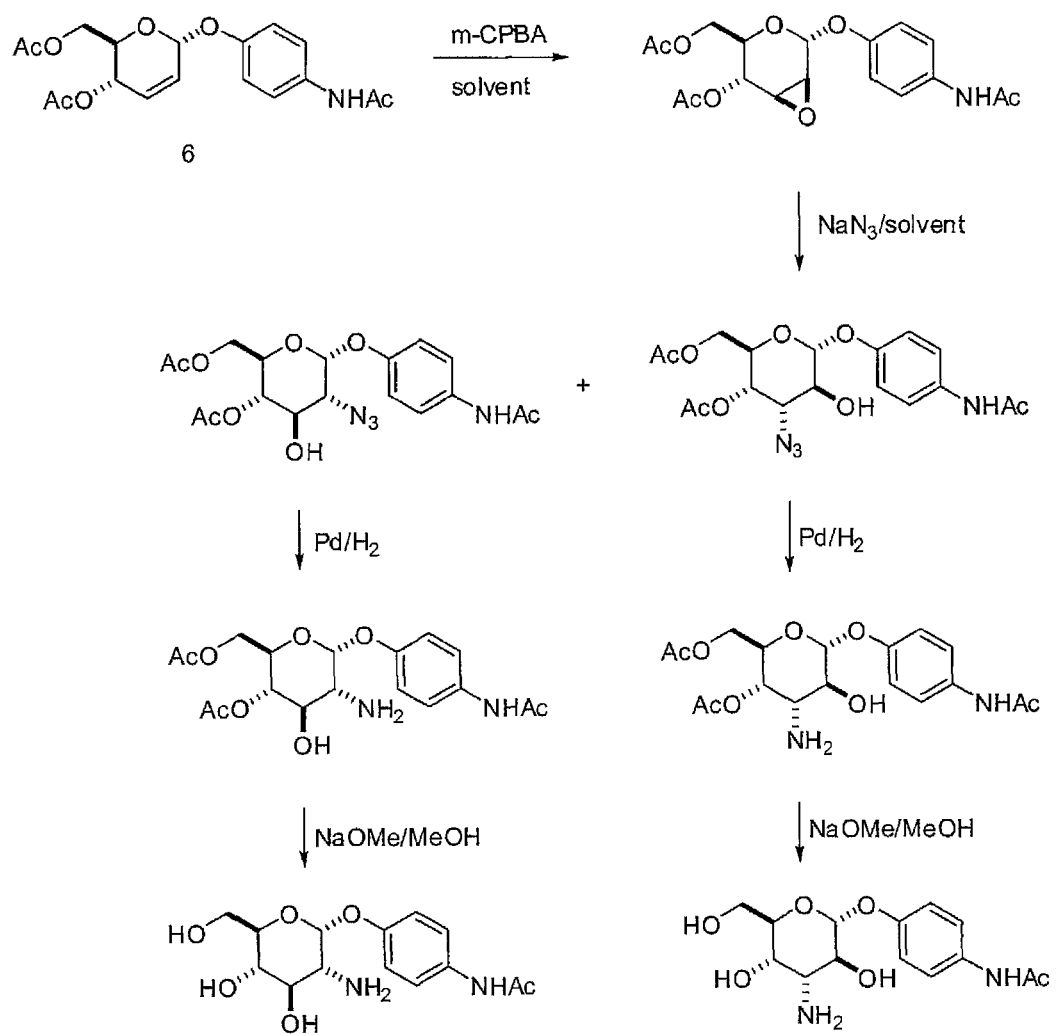

FIG. 13 shows a specific schematic of a synthetic route specific to compound 6.

Figure 14:
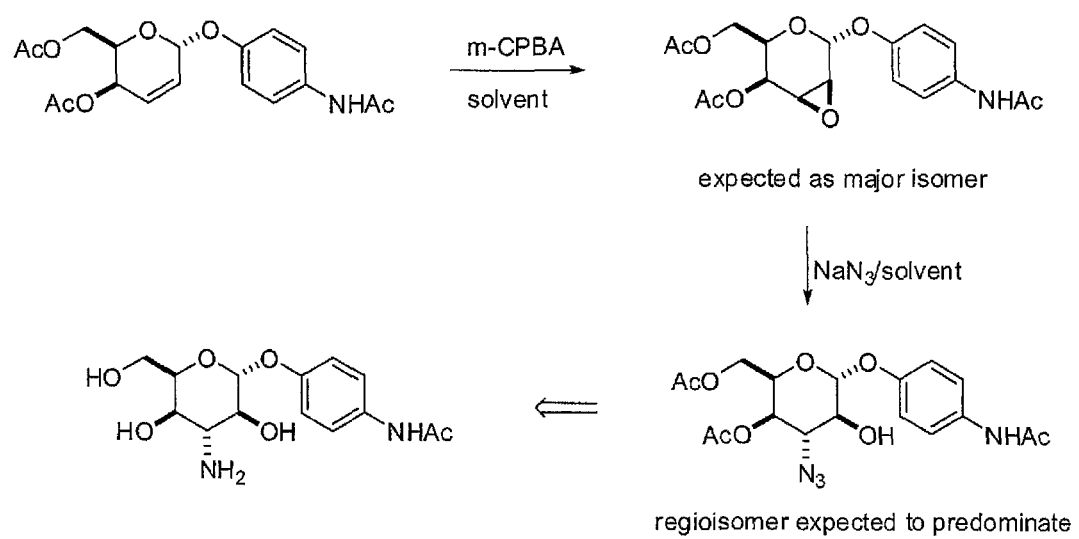

FIG. 14 shows a specific schematic of a synthetic route specific to the 3-amino analog.

Figure 15:
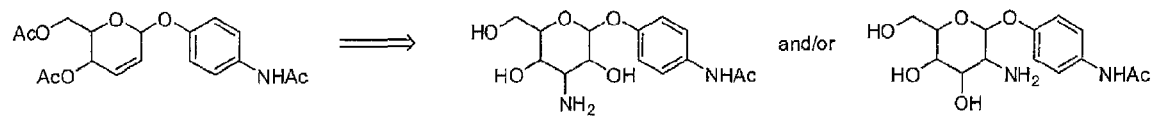

FIG. 15 shows a specific schematic showing the 2,3-olefin can provide the 2- or 3-amino sugar analogs.

Figure 16:
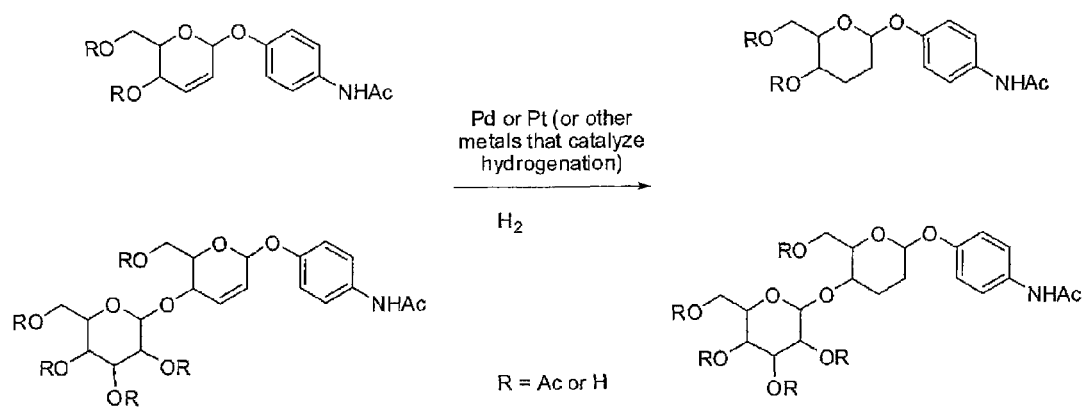

FIG. 16 shows a specific schematic of hydrogenation of 2,3 olefin acetaminophen analogs. FIG. 16 shows the method with both the monosaccharide and disaccharide analogs (general structures shown only, no stereochemistry specified); it should be noted that this reaction can be done either before (R=Ac) or after (R=H) hydrolysis of the protecting esters.

Table 1 shows the solubility of various acetaminophen analogs.

Table 2 shows a study of the time to % hydrolysis (in days) of various acetaminophen analogs at various pD (pH in D$_2$O).

Table 3 shows the details of the pharmacokinetics study selected glycosylated acetaminophen analogs.

Table 4 shows the mean concentration of the pro-drug in rat plasma or blood after intravenous administration (nmol/L).

Table 5 shows the mean concentration of acetaminophen in rat plasma or blood after intravenous administration (nmol/L).

Table 6 shows the brain to plasma ratio of acetaminophen after intravenous dosing of acetaminophen, analog 5 or analog 8.

DEFINITIONS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, "acetaminophen" refers to a compound represented by the following chemical structure:

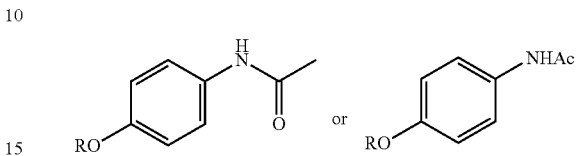

where R is H. It is not intended that the invention be limited to any particular derivative, analog or isomer of acetaminophen or salt thereof. Examples of derivatives of acetaminophen include but are in no way limited to acetaminophen or glycoside derivatives of acetaminophen. It is not intended that the present invention be limited by the type of chemical substituent or substituents that is or are coordinated to acetaminophen. Examples of chemical substituents include but are in no way limited to hydrogen, methyl, ethyl, formyl, acetyl, phenyl, chloride, bromide, hydroxyl, methoxyl, ethoxyl, methylthiol, ethylthiol, propionyl, carboxyl, methoxy carbonyl, ethoxycarbonyl, methylthiocarbonyl, ethylthiocarbonyl, butylthiocarbonyl, dimethylcarbamyl, diethylcarbamyl, N-piperidinylcarbonyl, N-methyl-N'-piperazinylcarbonyl, 2-(dimethylamino)ethylcarboxy, N-morpholinylcarbonyl, 2-(dimethylamino)ethylcarbamyl, 1-piperidinylcarbonyl, methylsulfonyl, ethylsulfonyl, phenylsulfonyl, 2-piperidinylethyl, 2-morpholinylethyl, 2-(dimethylamino)ethyl, 2-(diethylamino)ethyl, butylthiol, dimethylamino, diethylamino, piperidinyl, pyrrolidinyl, imidazolyl, pyrazolyl, N-methylpiperazinyl and 2-(dimethylamino)ethylamino.

"Epimers" refer to diastereomers that differ in configuration of only one stereogenic center. Diastereomers are a class of stereoisomers that are non-superposable, non-mirror images of one another, unlike enantiomers that are non-superposable mirror images of one another.

"Anomers" refer to a special type of epimer. It is a stereoisomer (diastereomer, more precisely) of a cyclic saccharide that differs only in its configuration at the hemiacetal or hemiketal carbon, also called the anomeric carbon.

Anomers are identified as "α" or "β" based on the relation between the stereochemistry of the exocyclic oxygen atom at the anomeric carbon and the oxygen attached to the configurational atom (defining the sugar as D or L), which is often the furthest chiral centre in the ring. The α anomer is the one in which these two positions have the same configuration; they are opposite in the β anomer.

For example in the case of α-D-glucopyranose vs. β-D-glucopyranose have the structures, respectively:

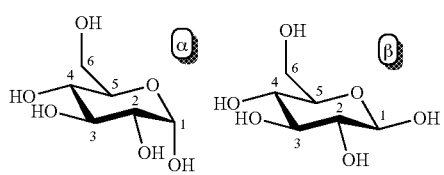

Unless otherwise stated, it can be assumed the current invention contemplates both α and β anomers described.

"Sugar" refers to a monosaccharide, disaccharide, trisaccharides, or polysaccharides. Monosaccharides have the general formula $(CH_2O)_n$, in which n is an integer larger than 2. Disaccharides have the general formula $C_n(H_2O)_{n-1}$, with n larger than 5. Polysaccharides include such substances as cellulose, dextrin, glycogen, and starch.

A "pharmaceutically acceptable monosaccharide" is a pharmaceutically acceptable aldose sugar, a pharmaceutically acceptable ketose sugar, or other specified sugar. Among the pharmaceutically acceptable aldose sugars within the contemplation of the present invention are erythrose, threose, ribose, arabinose, xylose, lyxose, allose, altrose, glucose, mannose, gulose, idose, galactose and talose. Among the pharmaceutically acceptable ketose sugars preferred for use in the composition of the present invention are erythrulose, ribulose, xylulose, psicose, fructose, sorbose, tagatose, and sedoheptulose. Among the other specified sugars preferred for use in the composition of the present invention are fucose, fuculose, rhamnose, or any other deoxy sugar. Although either (D) or (L) isomers may be employed, the (D) form is generally preferable.

The present disaccharide derivatives are preferably derived from disaccharides of the general formula $C_{12}H_{22}O_{11}$ and may suitably be chosen from the group consisting of cellobiose, gentiobiose, lactose, lactulose, maltose, melibiose, sucrose, trehalose, and turanose. Preferably, the novel disaccharide derivatives are derived from lactose, maltose or sucrose.

The pharmaceutical compositions of the present invention may be prepared by formulating them in dosage forms which are suitable for peroral, rectal or nonparenteral administration, the last-mentioned including intravenous injection and administration into the cerebrospinal fluid. For this purpose, common carriers and routine formulation techniques may be employed.

"Common carriers" means those which are employed in standard pharmaceutical preparations and includes excipients, binders and disintegrators the choice of which depends on the specific dosage form used. Typical examples of the excipient are starch, lactose, sucrose, glucose, mannitol and cellulose; illustrative binders are polyvinylpyrrolidone, starch, sucrose, hydroxypropyl cellulose and gum arabic; illustrative disintegrators include starch, agar, gelatin powder, cellulose, and CMC. Any other common excipients, binders and disintegrators may also be employed.

In addition of the carriers described above, the pharmaceutical composition of the present invention preferably contains antioxidants for the purpose of stabilizing the effective ingredient. Appropriate antioxidants may be selected from among those which are commonly incorporated in pharmacueticals and include ascorbic acid, N-acetyleystein, L-cystein, dl-α-tocopherol, and natural tocopherol.

Formulations of the pharmaceutical composition of the present invention which are suitable for peroral administration may be provided in the form of tablets, capsules, powders, granules, or suspensions in non-aqueous solutions such as syrups, emulsions or drafts, each containing one or more of the active compounds in predetermined amounts.

The granule may be provided by first preparing an intimate mixture of one or more of the active ingredients with one or more of the auxiliary components shown above, then granulating the mixture, and classifying the granules by screening through a sieve.

The tablet may be prepared by compressing or otherwise forming one or more of the active ingredients, optionally with one or more auxiliary components.

The capsule may be prepared by first making a powder or granules as an intimate mixture of one or more of the active ingredients with one or more auxiliary components, then charging the mixture into an appropriate capsule on a packing machine, etc.

The pharmaceutical composition of the present invention may be formulated as a suppository (for rectal administration) with the aid of a common carrier such a cocoa butter. The pharmaceutical composition of the present invention may also be formulated in a dosage form suitable for non-parenteral administration by packaging one or more active ingredients as dry solids in a sterile nitrogenpurged container. The resulting dry formulation may be administered to patients non-parenterally after being dispersed or dissolved in a given amount of aseptic water.

The dosage forms are preferably prepared from a mixture of the active ingredients, routine auxiliary components and one or more of the antioxidants listed above. If desired, the formulations may further contain one or more auxiliary components selected from among excipients, buffers, flavoring agents, binders, surfactants, thickening agents, and lubricants.

The dose of the acetaminophen pro-drug will of course vary with the route of administration, the severity of the disease to be treated, and the patient to be treated, but the exact dose ultimately chosen should be left to the good discretion of the doctor responsible for the treatment. If a desired dose is determined, the active ingredient may be administered once a day or, alternatively, it may be administered in up to four portions daily at suitable intervals. The active ingredient may be straightforwardly administered without being mixed with any other components. However, for several reasons, typically for the purpose of providing ease in controlling the dose level, the active compound is preferably administered in a pharmaceutical dosage form.

The term "salts", as used herein, refers to any salt that complexes with identified compounds contained herein while retaining a desired function, e.g., biological activity. Examples of such salts include, but are not limited to, acid addition salts formed with inorganic acids (e.g. hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid. Unless otherwise specifically stated, the present invention contemplates pharmaceutically acceptable salts of the considered pro-drugs.

As used herein, "hydrogen" means —H; "hydroxy" means —OH; "oxo" means =O; "halo" means independently —F, —Cl, —Br or —I; "amino" means —$NH_2$ (see below for definitions of groups containing the term amino, e.g., alkylamino); "hydroxyamino" means —NHOH; "nitro" means —$NO_2$; imino means =NH (see below for definitions of groups containing the term imino, e.g., alkylamino); "cyano" means —CN; "azido" means —$N_3$; "mercapto" means —SH; "thio" means =S; "sulfonamido" means —NHS(O)$_2$— (see below for definitions of groups containing the term sulfonamido, e.g., alkylsulfonamido); "sulfonyl" means —S(O)$_2$— (see below for definitions of groups containing the term sulfonyl, e.g., alkylsulfonyl); and "silyl" means —$SiH_3$ (see below for definitions of group(s) containing the term silyl, e.g., alkylsilyl).

As used herein, "olefin" means any of a class of unsaturated hydrocarbon containing one or more pairs of carbon atoms linked by a double bond (see covalent bond, saturation). Olefins may be classified by whether the double bond is in a ring (cyclic) or a chain (acyclic, or aliphatic) or by the number of double bonds (monoolefin, diolefin, etc.).

As used herein, "methylene" means a chemical species in which a carbon atom is bonded to two hydrogen atoms. The —CH$_2$— group is considered to be the standard methylene group. Methylene groups in a chain or ring contribute to its size and lipophilicity. In this context dideoxy also refers the methylene groups. In particular a 2,3-dideoxy compound is the same as 2,3-methylene (2,3-methylene-glycoside=2,3-dideoxy-glycoside).

For the groups below, the following parenthetical subscripts further define the groups as follows: "(Cn)" defines the exact number (n) of carbon atoms in the group; "(C≤n)" defines the maximum number (n) of carbon atoms that can be in the group; (Cn-n') defines both the minimum (n) and maximum number (n') of carbon atoms in the group. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3-10 carbon atoms)). Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3-10 carbon atoms)).

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_2$C(O)NH$_2$, —CH$_2$C(O)NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$.

The term "alkanediyl" when used without the "substituted" modifier refers to a non-aromatic divalent group, wherein the alkanediyl group is attached with two σ-bonds, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

are non-limiting examples of alkanediyl groups. The term "substituted alkanediyl" refers to a non-aromatic monovalent group, wherein the alkynediyl group is attached with two σ-bonds, with one or two saturated carbon atom(s) as the point(s) of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkanediyl groups: —CH(F)—, —CF$_2$—, —CH(Cl)—, —CH(OH)—, —CH(OCH$_3$)—, and —CH$_2$CH(Cl)—.

The term "alkenyl" when used without the "substituted" modifier refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "substituted alkenyl" refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH=CHF, —CH=CHCl and —CH=CHBr, are non-limiting examples of substituted alkenyl groups.

The term "alkenediyl" when used without the "substituted" modifier refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

are non-limiting examples of alkenediyl groups. The term "substituted alkenediyl" refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and at least one atom independently selected from the group consisting of N, O, F, Cl, Br, I, Si, P, and S. The following groups are non-limiting examples of substituted alkenediyl groups: —CF=CH—, —C(OH)=CH—, and —CH$_2$CH=C(Cl)—.

The term "alkynyl" when used without the "substituted" modifier refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH$_3$, —C≡CC$_6$H$_5$ and —CH$_2$C≡CCH$_3$, are non-limiting examples of alkynyl groups. The term "substituted alkynyl" refers to a monovalent group with a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡CSi(CH₃)₃, is a non-limiting example of a substituted alkynyl group.

The term "alkynediyl" when used without the "substituted" modifier refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and no atoms other than carbon and hydrogen. The groups, —C≡CCH₂—, and —C≡CCH(CH₃)— are non-limiting examples of alkynediyl groups. The term "substituted alkynediyl" refers to a non-aromatic divalent group, wherein the alkynediyl group is attached with two r-bonds, with two carbon atoms as points of attachment, a linear or branched, cyclo, cyclic or acyclic structure, at least one carbon-carbon triple bond, and at least one atom independently selected from the group consisting of N, O, F, Cl, Br, I, Si, P, and S. The groups —C≡CCFH— and —C≡CHCH(Cl)— are non-limiting examples of substituted alkynediyl groups.

The term "aryl" when used without the "substituted" modifier refers to a monovalent group with an aromatic carbon atom as the point of attachment, said carbon atom forming part of a six-membered aromatic ring structure wherein the ring atoms are all carbon, and wherein the monovalent group consists of no atoms other than carbon and hydrogen. Non-limiting examples of aryl groups include phenyl (Ph), methylphenyl, (dimethyl)phenyl, —C₆H₄CH₂CH₃ (ethylphenyl), —C₆H₄CH₂CH₂CH₃ (propylphenyl), —C₆H₄CH(CH₃)₂, —C₆H₄CH(CH₂)₂, —C₆H₃(CH₃)CH₂CH₃ (methylethylphenyl), —C₆H₄CH═CH₂ (vinylphenyl), —C₆H₄CH═CHCH₃, —C₆H₄C≡CH, —C₆H₄C≡CCH₃, naphthyl, and the monovalent group derived from biphenyl. The term "substituted aryl" refers to a monovalent group with an aromatic carbon atom as the point of attachment, said carbon atom forming part of a six-membered aromatic ring structure wherein the ring atoms are all carbon, and wherein the monovalent group further has at least one atom independently selected from the group consisting of N, O, F, Cl, Br, I, Si, P, and S, Non-limiting examples of substituted aryl groups include the groups: —C₆H₄F, —C₆H₄Cl, —C₆H₄Br, —C₆H₄I, —C₆H₄OH, —C₆H₄OCH₃, —C₆H₄OCH₂CH₃, —C₆H₄OC(O)CH₃, C₆H₄NH₂, —C₆H₄NHCH₃, —C₆H₄N(CH₃)₂, —C₆H₄CH₂OH, —C₆H₄CH₂OC(O)CH₃, —C₆H₄CH₂NH₂, —C₆H₄CF₃, —C₆H₄CN, —C₆H₄CHO, —C₆H₄CHO, —C₆H₄C(O)CH₃, —C₆H₄C(O)C₆H₅, —C₆H₄CO₂H, —C₆H₄CO₂CH₃, —C₆H₄CONH₂, —C₆H₄CONHCH₃, and —C₆H₄CON(CH₃)₂.

The term "arenediyl" when used without the "substituted" modifier refers to a divalent group, wherein the arenediyl group is attached with two σ-bonds, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of arenediyl groups include:

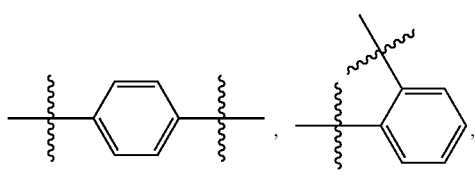

-continued

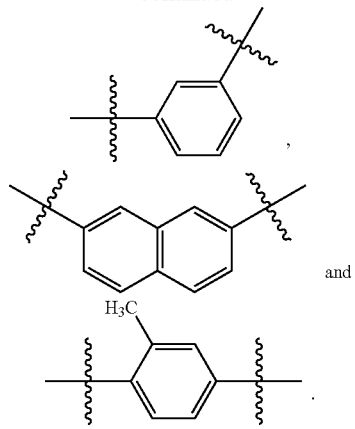

The term "substituted arenediyl" refers to a divalent group, wherein the arenediyl group is attached with two σ-bonds, with two aromatic carbon atoms as points of attachment, said carbon atoms forming part of one or more six-membered aromatic rings structure(s), wherein the ring atoms are all carbon, and wherein the divalent group further has at least one atom independently selected from the group consisting of N, O, F, Cl, Br, I, Si, P, and S.

The term "aralkyl" when used without the "substituted" modifier refers to the monovalent group-alkanediyl-aryl, in which the terms alkanediyl and aryl are each used in a manner consistent with the definitions provided above. Non-limiting examples of aralkyls are: phenylmethyl (benzyl, Bn), 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms. When the term "aralkyl" is used with the "substituted" modifier, either one or both the alkanediyl and the aryl is substituted. Non-limiting examples of substituted aralkyls are: (3-chlorophenyl)-methyl, 2-oxo-2-phenyl-ethyl (phenylcarbonylmethyl), 2-chloro-2-phenyl-ethyl, chromanyl where the point of attachment is one of the saturated carbon atoms, and tetrahydroquinolinyl where the point of attachment is one of the saturated atoms.

The term "heteroaryl" when used without the "substituted" modifier refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). The term "substituted heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, Cl, Br, I, Si, and P.

The term "heteroarenediyl" when used without the "substituted" modifier refers to a divalent group, wherein the heteroarenediyl group is attached with two σ-bonds, with an aromatic carbon atom or nitrogen atom as the point of attachment, said carbon atom or nitrogen atom two aromatic atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of heteroarenediyl groups include:

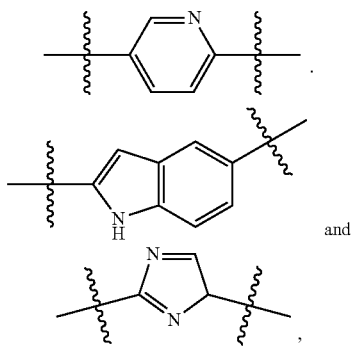

The term "substituted heteroarenediyl" refers to a divalent group, wherein the heteroarenediyl group is attached with two σ-bonds, with two aromatic carbon atoms as points of attachment, said carbon atoms forming part of one or more six-membered aromatic rings structure(s), wherein the ring atoms are all carbon, and wherein the divalent group further has at least one atom independently selected from the group consisting of N, O, F, Cl, Br, I, Si, P, and S.

The term "heteroaralkyl" when used without the "substituted" modifier refers to the monovalent group-alkanediyl-heteroaryl, in which the terms alkanediyl and heteroaryl are each used in a manner consistent with the definitions provided above. Non-limiting examples of aralkyls are: pyridylmethyl, and thienylmethyl. When the term "heteroaralkyl" is used with the "substituted" modifier, either one or both the alkanediyl and the heteroaryl is substituted.

The term "acyl" when used without the "substituted" modifier refers to a monovalent group with a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —C(O)CH$_3$, —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, —COC$_6$H$_3$(CH$_3$)$_2$, and —C(O)CH$_2$C$_6$H$_5$, are non-limiting examples of acyl groups. The term "acyl" therefore encompasses, but is not limited to groups sometimes referred to as "alkyl carbonyl" and "aryl carbonyl" groups. The term "substituted acyl" refers to a monovalent group with a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —C(O)CH$_2$CF$_3$, —CO$_2$H (carboxyl), —CO$_2$CH$_3$ (methylcarboxyl), —CO$_2$CH$_2$CH$_3$, —CO$_2$CH$_2$CH$_2$CH$_3$, —CO$_2$C$_6$H$_5$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, —CONHCH$_2$CF$_3$, —CO-pyridyl, —CO-imidazoyl, and —C(O)N$_3$, are non-limiting examples of substituted acyl groups. The team "substituted acyl" encompasses, but is not limited to, "heteroaryl carbonyl" groups.

The term "alkylidene" when used without the "substituted" modifier refers to the divalent group =CRR', wherein the alkylidene group is attached with one σ-bond and one π-bond, in which R and R' are independently hydrogen, alkyl, or R and R' are taken together to represent alkanediyl. Non-limiting examples of alkylidene groups include: =CH$_2$, =CH(CH$_2$CH$_3$), and =C(CH$_3$)$_2$. The term "substituted alkylidene" refers to the group =CRR', wherein the alkylidene group is attached with one σ-bond and one π-bond, in which R and R' are independently hydrogen, alkyl, substituted alkyl, or R and R' are taken together to represent a substituted alkanediyl, provided that either one of R and R' is a substituted alkyl or R and R' are taken together to represent a substituted alkanediyl.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The term "substituted alkoxy" refers to the group —OR, in which R is a substituted alkyl, as that term is defined above. For example, —OCH$_2$CF$_3$ is a substituted alkoxy group.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

In structures wherein stereochemistry is not explicitly indicated, it is assumed that either stereochemistry is considered and both isomers claimed.

Any undefined valency on an atom of a structure shown in this application implicitly represents a hydrogen atom bonded to the atom.

The term "protecting group," as that term is used in the specification and/or claims, is used in the conventional chemical sense as a group, which reversibly renders unreactive a functional group under certain conditions of a desired reaction and is understood not to be H. After the desired reaction, protecting groups may be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment. It should be noted that the functionality protected by the protecting group may or may not be a part of what is referred to as the protecting group.

Protecting groups include but are not limited to: alcohol protecting groups: acetoxy group, acetate (AC), β-methoxyethoxymethyl ether (MEM), methoxymethyl ether (MOM), p-methoxybenzyl ether (PMB), methylthiomethyl ether, pivaloyl (Piv), tetrahydropyran (THP), silyl ethers (including but not limited to trimethylsilyl (TMS), tert-butyldimethylsilyl (TBDMS), and triisopropylsilyl (TIPS) ethers), methyl ethers, and ethoxyethyl ethers (EE). Amine protecting groups: carbobenzyloxy (Cbz) group, p-methoxybenzyl carbonyl (Moz or MeOZ) group, tert-butyloxycarbonyl (BOC) group, 9-fluorenylmethyloxycarbonyl (FMOC) group, benzyl (Bn) group, p-methoxybenzyl (PMB), dimethoxybenzyl (DMPM), p-methoxyphenyl (PMP) group, tosyl (Ts) group, and other sulfonamides (Nosyl & Nps) groups. Carbonyl protecting groups: acetals, ketals, acylals, and dithianes. Carboxylic acid protecting groups: alkyl esters, aryl esters, silyl esters. Protection of terminal alkynes protected as propargyl alcohols in the Favorskii reaction. These and other considered protecting groups are described in the book on protecting groups by Wuts and Greene [5].

The term "leaving group," as that term is used in the specification and/or claims, is an atom or group (charged or uncharged) that becomes detached from an atom in what is considered to be the residual or main part of the substrate in a specified reaction.

Leaving groups include, but are not limited to: $NH_2^-$ (amine), $CH_3O^-$ (methoxy), $HO^-$ (hydroxyl), $CH_3COO^-$ (carboxylate), $H_2O$ (water), $F^-$, $Cl^-$, $I^-$, $N_3^-$ (azide), $SCN^-$ (thiocyanate), $NO_2$ (nitro), tosyl (Ts) groups, and protecting groups.

The use of the word "a" or "an," when used in conjunction with the term "comprising" in the claims and/or the specification may mean "one," but it is also consistent with the meaning of "one or more," "at least one," and "one or more than one."

Throughout this application, the terms "about" or "approximately" are used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, or hoped for result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As used herein, the term "pro-drug" refers to a pharmacological substance (drug) that is administered in an inactive (or significantly less active) form. Once administered, the pro-drug is metabolised in vivo into an active metabolite. The rationale behind the use of a pro-drug is generally for absorption, distribution, metabolism, and excretion (ADME) optimization. Pro-drugs are usually designed to improve oral bioavailability, with poor absorption from the gastrointestinal tract usually being the limiting factor. Additionally, the use of a pro-drug strategy increases the selectivity of the drug for its intended target.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylicacids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002) [6]. Unless otherwise specifically stated, the present invention contemplates pharmaceutically acceptable salts of the considered pro-drugs.

As used herein, "predominantly one enantiomer" means that a compound contains at least about 85% of one enantiomer, or more preferably at least about 90% of one enantiomer, or even more preferably at least about 95% of one enantiomer, or most preferably at least about 99% of one enantiomer. Similarly, the phrase "substantially free from other optical isomers" means that the composition contains at most about 15% of another enantiomer or diastereomer, more preferably at most about 10% of another enantiomer or diastereomer, even more preferably at most about 5% of another enantiomer or diastereomer, and most preferably at most about 1% of another enantiomer or diastereomer.

As used herein, "predominantly one anomer" means that a compound contains at least about 85% of one anomer, or more preferably at least about 90% of one anomer, or even more preferably at least about 95% of one anomer, or most preferably at least about 99% of one anomer. Similarly, the phrase "substantially free from other optical isomers" means that the composition contains at most about 15% of another anomer, more preferably at most about 10% of another anomer, even more preferably at most about 5% of another anomer, and most preferably at most about 1% of another anomer.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers.

Enantiomers are compounds that individually have properties said to have "optical activity" and consist of chiral molecules. If a chiral molecule is dextrorotary, its enantiomer will be levorotary, and vice-versa. In fact, the enantiomers will rotate polarized light the same number of degrees, but in opposite directions. "Dextrorotation" and "levorotation" (also spelled laevorotation) refer, respectively, to the properties of rotating plane polarized light clockwise (for dextrorotation) or counterclockwise (for levorotation). A compound with dextrorotation is called "dextrorotary," while a compound with levorotation is called "levorotary".

A standard measure of the degree to which a compound is dextrorotary or levorotary is the quantity called the "specific rotation" "$[\alpha]$". Dextrorotary compounds have a positive specific rotation, while levorotary compounds have negative. Two enantiomers have equal and opposite specific rotations. A dextrorotary compound is prefixed "(+)-" or "d-". Likewise, a levorotary compound is often prefixed "(−)-" or "l-". These "d-" and "l-" prefixes should not be confused with the "D-" and "L-" prefixes based on the actual configuration of each enantiomer, with the version synthesized from naturally occurring (+)-compound being considered the D-form. A mixture of enantiomers of the compounds is prefixed "(±)-". An equal mixture of enantiomers of the compounds is considered "optically inactive".

The invention contemplates that for any stereocenter or axis of chirality for which stereochemistry has not been defined, that stereocenter or axis of chirality can be present in its R form, S form, or as a mixture of the R and S forms, including racemic and non-racemic mixtures.

The present invention contemplates the above-described compositions in "therapeutically effective amounts" or "pharmaceutically effective amounts", which means that amount which, when administered to a subject or patient for treating a disease, is sufficient to effect such treatment for the disease or to emeliorate one or more symptoms of a disease or condition (e.g. emeliorate pain).

The above definitions supersede any conflicting definition in any of the reference that is incorporated by reference herein.

As used herein, the terms "treat" and "treating" are not limited to the case where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

"Subject" refers to any mammal, preferably a human patient, livestock, or domestic pet.

In a specific embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents can be used. When administered to a subject, the pharmaceutically acceptable vehicles are preferably sterile. Water can be the vehicle when the active compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The present compositions, if desired, can also contain minor amounts of wetting or emulsifying agents, or pH buffering agents. Pharmaceutically acceptable sugars include but are not limited to sucrose, dextrose, maltose, galactose, rhamnose, and lactose. Pharmaceutically acceptable sugar alcohols include but are not limited to mannitol, xylitol, and sorbitol.

ABBREVIATIONS $C_0$—Initial concentration at time 0, extrapolated.
$t_{1/2}$—Half-life of the pro-drug analog (Table 4) or acetaminophen from the pro-drug (Table 5).
$CL_p$—Estimate of tatal body clearance, $CL_p$=dose/$AUC_{inf}$
$Vd_{ss}$—Estimate of the volume of distribution; $Vd_{ss}$=dose/$AUC_{inf}$
$AUC_{last}$—Area under the curve of time versus concentration, to the last detected concentration
$AUC_{inf}$—Area under the curve of time versus concentration, with concentration extrapolated to infinity
$MRT_{inf}$—Mean Residence Time when the drug concentration profile is extrapolated to infinity.
LLOQ—Low limit of quantitation
n.d.—Not detected

EXAMPLES

The following examples are provided in order to demonstrate and further illustrate certain preferred embodiments and aspects of the present invention and are not to be construed as limiting the scope thereof.

Example I

Solubility and Solution Stability Study of Some of the Analogs

The water solubility of some of the analogs prepared was determined and shown in Table 1. The method use involved stirring the sample in $D_2O$ for a period of 3 days, followed by filtration using a 0.2µ syringe filter. A measured volume of this saturated solution was diluted with a standard solution of DSS in $D_2O$, and a $^1H$ NMR was taken. Integration of the DSS peaks compared to that of the analog would allow for the determination of its concentration, and thus the concentration of the saturated solution. As a check, the solubility of acetaminophen was found to be 13 mg/mL, in good agreement with the literature value of 14 mg/mL.

The disaccharide analog 5 had the highest solubility of all of the analogs; however, it should be noted that the 6-acetylmannose (monosaccharide) analog 16 also has excellent solubility as well.

A stability study at three different pH's (actually pD since the study is being conducted in $D_2O$) is also being performed on two of the analogs (glucal 1 and maltal 2) from the original patent, as well as on acetaminophen itself, mannose analog 8, glucose-mannose 5, and the reduced glucal analog, 2,3-dideoxy glucose 12 (shown in Table 2). The 3 pD's were chosen since it is known that acetaminophen has it greatest stability at a pH of 6. The initial results show that the glucal 1 is the least stable to all of the pD's, followed closely by maltal 2. The 2,3-dideoxyglucose analog 12, although more stable than glucal 1 and maltal 2, is also showing a lot of instability to these conditions. Thus far, after 167 days of the study, the acetaminophen, mannose analog 8 and glucose-mannose analog 5 have shown no change in their $^1H$ NMR spectra.

Importantly, the solubility and stability studies have demonstrated that the analogs from the 1997 (U.S. Pat. No. 5,693,767) patent [1] are fairly unstable in water at 3 different pH's and that the new analogs that have been prepared have both higher solubility and great stability.

Method for Testing Stability:

10 mL (11.07 g) $D_2O$ was placed in 3 separate vials with a stir bar and 0.002 moles (0.272 g) monobasic potassium phosphate ($KH_2PO_4$) was added to each. With the pD metered, $NaOD/D_2O$ was added drop-wise to each to adjust the pD's to 5.0, 6.0, and 7.0. Each of these solutions was gently boiled before use. Thus each vial contained 0.2 mM phosphate buffered solution. A 0.01 mmole sample of each analog as well as acetaminophen itself was placed in a small vial and 0.3 mL pre-boiled $D_2O$ was added. The sample was sterilized by heating for 10 seconds, and after it had cooled down to ambient temperature (about 1 minute), 0.3 mL of one of the 0.2 mM 3 buffered solutions was added. The 0.6 mL sample was then placed in a sterilized NMR tube and the tube sealed and labeled. Each of the samples was stored at 23° C. protected from the light and monitored by $^1H$ NMR (64 scans for each sample) periodically.

Example II

Biological Evaluation of Selected Analogs

The pharmacokinetics of seven of the above-described analogs were studied in male Sprague-Dawley rats in order to determine how quickly the acetaminophen was released from the pro-drug and the concentration of acetaminophen in blood versus time. Administration for each was between 64.5 and 69.0 µmol/kg in either saline or water with a pH from 4-6 (Table 3). The half life of the mannose analog 8, 6-acetylmannose 15, 6-butyrylmannose 18 and 6-isobutyrylmannose 19 all had good half-lives ($t_{1/2}$), all significantly less than 1 hour (Table 4) and consequently, all have low values for AUC (area under curve of concentration versus time). Conversely, disaccharide 8, 6-succinate 20 and 6-deoxymannose 23 all had relatively high half-lives and high AUC values, indicating a longer-lived pro-drug in the system.

The concentration of acetaminophen released by each pro-drug (as well as when acetaminophen itself was dosed) over time is shown in Table 5. Importantly, the 6-acetylmannose analog 15 had the largest AUC value of all of the pro-drugs, and thus being the most efficient of these pro-drugs in releasing acetaminophen in the blood.

Finally, the concentration of acetaminophen in the brain over time was investigated for acetaminophen as well as for two of the pro-drug analogs, disaccharide 5 and mannose 8 (Table 6). This study confirmed that the monosaccharide 8 was much more efficient in delivering acetaminophen than disaccharide 5.

Example III

Synthesis of Acetaminophen Analog 15

The first step is glycosylation of 4-nitrophenol with a per-acylated carbohydrate (in the case shown, pentaacetyl mannose, but all carbohydrates should be claimed) with an acid catalyst ($BF_3OEt_2$ shown, but again, all others should be claimed) and solvent ($CH_2Cl_2$). The product from this reaction should give predominantly the α anomer.

The next three steps can be done in several different orders, but the order to the far right in FIG. 11 is probably the one to provide the best results. These steps consist of:

(1) Reduction of the nitro group with concomitant acylation to the amide. This can be affected with Pd and hydrogen gas in the presence of acetic anhydride.

(2) Hydrolysis of all of the acetates on the carbohydrate moiety. This can be accomplished by sodium methoxide in methanol, amongst others.

(3) Selective acylation of the C-6 hydroxyl. This will probably be best accomplished with the use of acetyl chloride and 2,4,6-collidine and a solvent (likely $CH_2Cl_2$).

Example IV

Synthesis of Amino Sugar Acetaminophen Analogs

Experimental

The idea here is that the olefin should be easily epoxidized, and this can be opened with a variety of nucleophiles, but azide would give us access to amino sugar analogs, and these would be new types of analogs (as opposed to opening with an oxygen nucleophile).

FIG. 13 shows a scheme that is specific to compound 6. Epoxidation would expected to take place almost exclusively from the face opposite the adjacent phenyl ring and 4-acetate. However, although nucleophilic ring attack of azide will occur from the bottom face only, there is a regio-chemical issue, whether it occurs at C-2 or C-3. Both would probably form and a mixture of diastereomers obtained (given that the phenoxy ring is a little larger, nucleophilic attack at C-3 would probably predominate, and the structure to the right in FIG. 13 would be the major isomer obtained).

Separation of the isomers, reduction of the azide to the amine, and hydrolysis of the acetates would complete the sequence.

If the stereochemistry at C-4 is reversed (i.e., the analog that would be obtained is tri-O-acetyl galactal were used in the glycosylation step), a mixture might be obtained for the epoxidation, but the one with the epoxide up would still likely predominate because the phenoxy ring is larger than the acetate and thus have a more controlling effect (it should be noted that both substituents are axial). So it is possible that azide attack at C-3 would predominate, thus ultimately leading to the 3-amino analog shown in FIG. 14. So, generally speaking, without taking into account the various stereochemical issues that depend on each individual sugar, analogs with the 2,3-olefin can provide the 2- or 3-amino sugar analogs shown in FIG. 15.

Example V

Hydrogenation

Essentially, there are a number of ways to reduce the 2,3 olefin, the most efficient and commonly used methods include hydrogenation with a metal catalyst such as Pd or Pt. FIG. 16 shows the method with both the monosaccharide and disaccharide analogs (general structures shown only, no stereochemistry specified); it should be noted that this reaction can be done either before (R=Ac) or after (R=H) hydrolysis of the protecting esters.

Example VI

Synthesis of Acetaminophen Analogs

Experimental

General.

$^1$H and $^{13}$C NMR spectra were taken on a Varian Mercury 300 or 400 MHz spectrometer. Chemical shifts are reported in parts per million (ppm) from an internal standard; either 2,2-dimethyl-2-silapentane-5-sulfonate sodium salt (DSS, for D$_2$O) or tetramethylsilane (TMS, for all other solvents) as an internal standard. Coupling constants (J values) are given in hertz (Hz). All chemicals were purchased from Sigma-Aldrich; all solvents were purchased from Pharmco-AAPER. THF was dried over sodium benzophenone ketyl and distilled, CH$_2$Cl$_2$ was dried over CaSO$_4$ and distilled. All reactions were monitored by thin-layer chromatography on silica gel 60 F254 (Merck); detection was carried out by UV and by charring after spraying with a solution made from 4.7 g Ceric ammonium sulfate and 5.6 mL concentrated sulfuric acid diluted to 100 mL. For flash column chromatography, silica gel 60, 230-400 mesh from Mallinckrodt was used. Optical rotations were measured on a Bellingham+Stanley ADP220 Parlarimeter at the concentration c specified in g/100 mL. Compound Characterization Data:

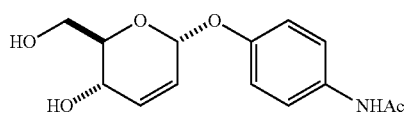 [SMILES: CC(=O)Nc1ccc(O[C@@H]2C=C[C@H](OC(C)=O)[C@@H](CO)O2)cc1]

1

Made in the manner described in U.S. Pat. No. 5,693,767 [1]. Compound 1: N-(4-(((2R,5S,6R)-5-hydroxy-6-(hydroxymethyl)-5,6-dihydro-2H-pyran-2-yloxy)phenyl)aceta- mide: $^1$H NMR (300 MHz, CDCl$_3$) δ 2.17 (s, 3H), 3.84 (s, 1H), 3.86 (s, 2H), 4.33 (m, 1H), 5.63 (d, J=4.7 Hz, 1H), 5.93 (1H) and 6.11 (1H) (ABq, J$_{AB}$=10.2 Hz; the peaks at 5.93 are further split into dd with J=0.5, 0.5 Hz) 7.04 (d, J=8.7 Hz, 2H), 7.40 (d, J=8.7 Hz, 2H); $^1$H NMR (300 MHz, DMSO) δ 2.09 (s, 3H), 3.71-3.88 (m, 4H), 4.16 (br d, J=6.0 Hz, 1H, OH), 4.43 (d, J=6.3 Hz, 1H, OH), 5.58 (dd, J=1.4, 1.4 Hz, 1H), 5.86 and 6.05 (1H) (ABq, J$_{AB}$=10.2 Hz; the peaks at 5.86 are further split into dd, J=2.2, 2.8 Hz; the peaks at 6.05 are further split into dd, J=1.4, 1.4 Hz), 7.04 (d, J=9.1 Hz, 2H), 7.53 (d, J=9.1 Hz, 2H), 9.17 (br s, 1H, NH); $^{13}$C NMR (75.5 MHz, DMSO) δ 23.8 (q), 60.5 (t), 61.9 (d), 73.5 (d), 93.3 (d), 117.8 (d, 2C), 120.3 (d, 2C), 124.6 (d), 133.9 (s), 135.5 (d), 152.9 (s), 167.8 (s).

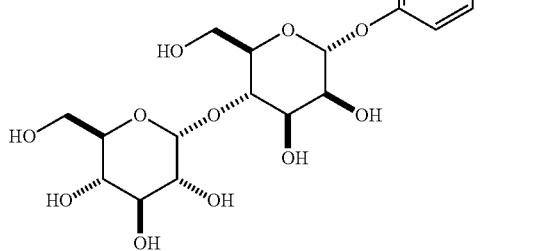

4

1-(4-acetaminophen)pentaacetyl-O-2,3-dideoxy, 2,3-didehydro maltose-2 (1.95 g) was dissolved in 10 mL water and 10 mL acetone and 0.438 g (1.25 equiv.) N-methyl 4-morpholone N-oxide and 0.29 mL of 4% OsO$_4$ in water (1.5 mol %) and the reaction was stirred overnight at room temperature. The reaction mixture was poured into 25 mL ethyl acetate and the organic layer was washed once each with 25 mL water and 20 mL brine. The organic layer was then dried over Na$_2$SO$_4$, filtered and the solvent removed under reduced pressure. Silica gel column chromatography (3:1 ethyl acetate/hexanes to ethyl acetate gradient) of the residue provided 1.97 g (96%) of the product 1-(4-acetaminophenoxy) pentaacetyl-O-acetyl 2-epi maltose 4 as a colorless oil. [α]$^{23}_D$ +149 (c 1.00, CH$_2$Cl$_2$); NMR (300 MHz, CDCl$_3$) δ 2.00 (s, 3H), 2.02 (s, 6H), 2.08 (s, 3H), 2.11 (s, 3H), 2.17 (s, 3H), 3.06 (v br s, 1H, OH), 3.25 (v br s, 1H, OH), 3.78-3.88 (m, 2H), 3.91-4.26 (m, 6H), 4.41 (d, J=11.0 Hz, 1H), 5.00 (dd, J=3.8, 10.5 Hz, 1H), 5.07 (dd, J=9.6, 9.6 Hz, 1H), 5.34 (d, J=3.6 Hz, 1H), 5.46 (s, 1H) (dd, J=9.6, 10.5 Hz, 1H), 7.02 (d, J=9.1 Hz, 2H), 7.40 (d, J=9.1 Hz, 2H); $^{13}$C NMR (75.5 MHz, CDCl$_3$) δ 20.9 (q), 61.9 (t), 63.4 (t), 68.4 (d), 69.3 (d), 69.9 (d), 70.4 (d), 70.7 (d), 71.2 (d), 76.6 (d), 78.3 (d), 98.0 (d), 100.4 (d), 117.1 (d, 2C), 122.1 (d, 2C), 132.8 (s), 152.8 (s), 169.2 (s), 169.7 (s), 170.4 (s), 170.5 (s), 170.9 (s), 171.0 (s).

5

1-(4-acetaminophenoxy)pentaacetyl-O-acetyl 2-epi maltose 4 (4.8 g) was dissolved in 50 mL methanol and sodium hydroxide (0.020 g, 7 mol %) added and stirred overnight. More methanol (25 mL) was added to dissolve the precipitate that had formed, and the mixture was run through a 4 cm column of Dowex CCR-3 weakly acidic ion exchange resin. The solvent was removed under reduced pressure, and purified by silica gel column chromatography (30% methanol/ethyl acetate) to provide the product 1-(4-acetaminophenoxy) 2-epi maltose 5 as a pure white solid which was then recrystallized from 20% methanol (added first to dissolve the product) 80% ethyl acetate (2.80 g, 84%). $[\alpha]^{23}_D$ +168 (c 1.00, H$_2$O); $^1$H NMR (300 MHz, D$_2$O) δ 2.19 (s, 3H), 3.45 (dd, J=9.1, 9.3 Hz, 1H), 3.64 (dd, J=3.6, 9.9 Hz, 1H), 3.70-3.90 (m, 6H), 3.96 (dd, J=9.2, 9.2 Hz, 1H), 4.20 (s, 1H), 4.33 (dd, J=3.0, 8.8 Hz, 1H), 5.40 (d, J=3.6 Hz, 1H), 5.62 (s, 1H), 7.19 (d, J=8.8 Hz, 2H), 7.39 (d, J=8.8 Hz, 2H); $^{13}$C NMR (75.5 MHz, D$_2$O) δ 25.4 (q), 63.2 (t), 63.3 (t), 72.0 (d), 72.6 (d), 73.6 (d), 74.5 (d, 2C), 75.4 (d), 75.7 (d), 78.1 (d), 100.9 (d), 102.9 (d), 120.1 (d, 2C), 126.0 (d, 2C), 134.6 (s), 155.4 (s), 175.2 (s).

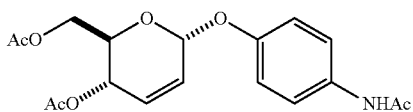

6

Made in the manner described in U.S. Pat. No. 5,693,767 [1]. Compound 6, (2R,3S,6R)-6-(4-acetamidophenoxy)-2-(acetoxymethyl)-3,6-dihydro-2H-pyran-3-yl acetate. $^1$H NMR (300 MHz, CDCl$_3$) δ 2.01 (s, 3H), 2.11 (s, 3H), 2.16 (s, 3H), 5.38 (d, J=8.5 Hz, 1H), 4.12-4.31 (m, 3H), 5.63 (s, 1H), 6.00 (1H) and 6.02 (1H) (ABq, J$_{AB}$=11.0 Hz; the peaks at 6.00 are further split into dd, J=0.8, 1.6 Hz) 7.07 (d, J=8.9 Hz, 2H), 7.20 (br s, 1H, NH), 7.41 (d, J=8.9 Hz, 2H); $^{13}$C NMR (75.5 MHz, CDCl$_3$) δ 20.8 (q), 21.1 (q), 24.4 (q), 62.8 (t), 65.2 (d), 67.8 (d), 93.5 (d), 117.7 (d, 2C), 121.7 (d, 2C), 127.2 (d), 130.2 (d), 133.1 (s), 153.8 (s), 168.7 (s), 170.4 (s), 170.9 (s).

8

[Structure of compound 8: HO-CH2-pyranose with OH groups and O-phenyl-NHAc]

1-(4'-acetamidophenoxy)-2,3-dideoxy 2,3-didehydro glucose 1 (3.36 g) was dissolved in 50 mL acetone and 2 mL water and N-methylmorpholone (1.70 g, 1.2 equiv) and osmium tetroxide (0.38 mL of 4% wt. % solution, 0.005 equivalents) was added and the reaction mixture stirred for 2 days. Silica gel column chromatography (15% methanol in acetone) was done directly on the reaction mixture providing the product as a white solid which was recrystallized (by dissolving the product in a minimum amount of boiling methanol and then adding boiling ethyl acetate until the solution turned opalescent) to provide 1-(4'-acetamidophenoxy) mannose 8 (2.68 g, 71%) as a pure white solid. $[\alpha]^{23}_D$ +116 (c 1.00, H$_2$O); $^1$H NMR (300 MHz, D$_2$O) δ 2.16 (s, 3H), 3.75 (m, 4H), 4.05 (br s, 1H), 4.18 (s, 1H), 5.61 (s, 1H), 7.17 (d, J=7.4 Hz, 2H), 7.36 (d, J=7.4 Hz, 2H); $^{13}$C NMR (75.5 MHz, D$_2$O) δ 25.4 (q), 63.4 (t), 69.2 (d), 72.6 (d, 2C), 73.0 (d), 76.0 (d), 101.1 (d), 120.2 (d, 2C), 126.2 (d, 2C) 134.6 (s), 155.5 (s), 175.3 (s).

10

[Structure of compound 10: AcO-pyranose with OAc group and O-phenyl-NHAc]

1-(4'-acetamidophenoxy)-di-O-acetyl-2,3-dideoxy 2,3-didehydro glucose 6 (6.5 g) was combined with sodium acetate (58.7 g, 40 equiv.) and toluene sulfonylhydrazine (30.0 g, 9 equiv.) in 75 mL DME and 75 mL water and the mixture heated to reflux for 3 hrs. The reaction mixture was cooled and poured into 500 mL ethyl acetate, and the solution washed once each with 500 mL water, 500 mL saturated NaHCO$_3$, 250 mL brine and dried over Na$_2$SO$_4$. The solution was filtered, the solvent removed under vacuum and silica gel column chromatography (2:1 ethyl acetate/hexanes) provided the product as an off-white solid. Recrystallization from 2:1 hexanes/ethyl acetate provided the product 1-(4'-acetamidophenoxy)-di-O-acetyl-2,3-dideoxy glucose 10 (4.3 g, 66%) as a pure white solid. $[\alpha]^{23}_D$ (c, CH$_2$Cl$_2$); $^1$H NMR (300 MHz, CDCl$_3$) δ 1.96-2.12 (m, 4H), 2.03 (s, 3H), 2.06 (s, 3H), 2.16 (s, 3H), 4.26 (dd, 11.9 Hz, 1H), 3.97-4.03 (m, 2H), 4.79-4.86 (m, 1H), 5.51 (br s, 1H), 7.05 (d, J=8.9 Hz, 2H), 7.20 (v br s, NH), 7.40 (d, J=8.9 Hz, 2H); $^{13}$C NMR (75.5 MHz, CDCl$_3$) δ 20.9 (q), 21.1 (q), 23.9 (t), 24.3 (q), 28.9 (t), 62.9 (t), 67.5 (d), 69.4 (d), 95.1 (d), 117.0 (d, 2C), 121.7 (d, 2C), 132.7 (s), 153.2 (s), 168.8 (s), 170.2 (s), 171.0 (s).

11

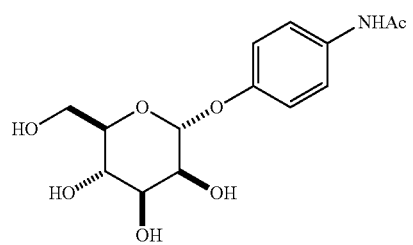

1-(4'-acetamidophenoxy)-penta-O-acetyl-2,3-dideoxy, 2,3-didehydro maltose 1 (10.0 g), sodium acetate (62.9 g, 50 equivalents) and toluene sulfonylhydrazide (28.6 g, 10 equivalents) were combined in 100 mL DME and 200 mL water and the reaction mixture heated to reflux for 3 hrs. The reaction mixture was poured into 500 mL ethyl acetate, and the mixture washed once each with 500 mL water, 500 mL saturated NaHCO$_3$, and 250 mL brine and then dried over Na$_2$SO$_4$. The solution was then filtered through a 2 inch plug of silica gel, and the solvent removed under vacuum. The resultant oil was recrystallized from 2:1 hexanes/ethyl acetate to provide 7.8 g (78%) of 1-(4'-acetamidophenoxy)-penta-O- acetyl-2,3-dideoxy maltose 11 as pure white needles. ¹H NMR (300 MHz, CDCl₃) δ 1.85-2.15 (m, 4H), 2.02 (s, 3H), 2.03 (s, 3H), 2.05 (s, 3H), 2.10 (s, 3H), 2.11 (s, 3H), 2.17 (s, 3), 3.65-3.77 (m, 1H), 3.96-4.01 (m, 2H), 4.07 (dd, J=2.3, 12.2 Hz, 1H), 4.2-4.32 (m, 3H), 4.83 (dd, J=3.8, 10.2 Hz, 1H), 5.10 (dd, J=9.4, 10.2 Hz), 5.30 (d, J=3.8 Hz, 1H), 5.40 (dd, J=9.4, 10.2 Hz, 1H), 5.47 (br s, 1H), 7.05 (d, J=8.9 Hz, 2H), 7.19 (br s, NH), 7.41 (d, J=8.9 Hz, 2H); ¹³C NMR (75.5 MHz, CDCl₃) δ 20.6 (q), 20.7 (q, 3C), 20.8 (q), 23.3 (t), 24.2 (q), 28.7 (t), 61.7 (t), 63.4 (t), 68.1 (d), 68.2 (d), 69.7 (d, 2C), 70.7 (d), 71.7 (d), 93.1 (d), 95.0 (d), 117.1 (d, 2C), 121.6 (d, 2C), 132.7 (s), 153.1 (s), 168.6 (s), 169.6 (s), 170.0 (s), 170.2 (s), 170.7 (s), 170.8 (s).

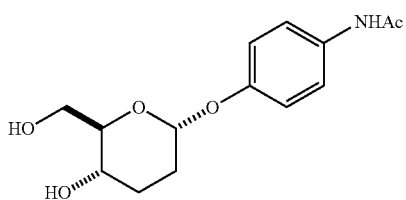

12

1-(4'-acetamidophenoxy)-di-O-acetyl-2,3-dideoxy glucose 10 (4.0 g) was dissolved in 50 mL methanol and sodium hydroxide (0.006 g) was added and the solution was stirred overnight. The mixture was then passed through a 4 cm column of Dowex CCR-3 (weakly acidic, H) ion exchange resin and the methanol removed under reduced pressure. The resultant solid was purified by recrystallization (dissolved in 30 mL hot methanol, then 200 mL hot ethyl acetate added) provide the product 1-(4'-acetamidophenoxy) 2,3-dideoxy glucose 12 (2.6 g, 84%) as a white solid. [α]²³_D +178 (c 1.00, CH₃OH); ¹H NMR (300 MHz, DMSO) δ 1.73-1.90 (m, 4H), 2.00 (s, 3H), 3.37-3.57 (m, 4H), 4.41 (dd, J=5.8, 6.0 Hz, OH) 4.83 (d, J=5.5 Hz, OH), 5.44 (s, 1H), 7.01 (d, J=8.8 Hz, 2H), 7.44 (d, J=8.8 Hz, 2H), 9.81 (s, NH); ¹³C NMR (75.5 MHz, DMSO) δ 23.7 (q), 26.9 (t), 28.9 (t), 60.9 (t), 64.5 (d), 75.2 (d), 94.8 (d), 117.0 (d, 2C), 120.2 (d, 2C), 133.4 (s), 152.3 (s), 167.7 (s).

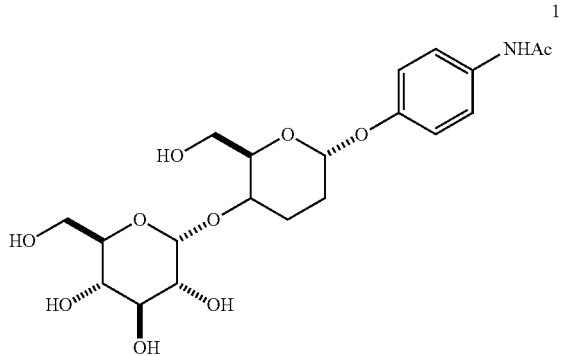

13

1-(4-acetamidophenoxy)-penta-O-acetyl-2,3-dideoxy maltose 11 (3.0 g) was dissolved in 50 mL methanol and sodium hydroxide (0.040 g) added and the solution was stirred at rt overnight. More methanol (25 mL) was added to dissolve the precipitated that formed, and the solution was passed through a 4 cm column of Dowex CCR-3 ion exchange resin (weakly acidic, hydrogen). The solvent was removed under vacuum and the solid recrystallized from 20% methanol/ethyl acetate (methanol first to dissolve the solid) to provide 1.75 g (86%) 1-(4-acetamidophenoxy)-2,3-dideoxy maltose 13 as a white solid. [α]²³_D(c, H₂O); ¹H NMR (300 MHz, D₂O) δ 1.82-1.97 (m, 2H), 2.10-2.15 (m, 1H), 2.14 (s, 3H), 2.24 (br d, J=9.6 Hz, 1H), 3.44 (dd, J=9.1, 9.9 Hz, 1H), 3.57 (dd, J=3.7, 9.9 Hz), 3.63-3.91 (m, 7H), 3.66 D, J=9.3 Hz, 1H), 5.17 (d, J=3.9 Hz, 1H), 5.65 (s, 1H), 7.15 (d, J=8.8 Hz, 2H), 7.35 (d, J=8.8 Hz, 2H); ¹³C NMR (75.5 MHz, D₂O) δ 24.4 (t), 25.4 (q), 30.5 (t), 63.0 (t), 63.2 (t), 70.9 (d), 72.0 (d), 73.6 (d), 74.9 (d, 2C), 75.6 (d), 96.6 (d), 98.2 (d), 120.3 (d, 2C), 125.7 (d, 2C), 134.4 (s), 155.7 (s), 174.9 (s).

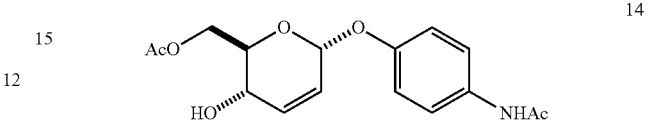

14

1-(4'-acetamidophenoxy)-4,6-di-O-acetyl-2,3-dideoxy 2,3-didehydro glucose 6 (0.050 g) was dissolved in 2 mL methanol and 1 mL THF and 2 mL of water containing 0.005 g NaHCO₃ was added and the solution was stirred at room temperature overnight. TLC indicated the presence of both diol 1 and monoacetate 14. Ethyl acetate (10 mL) was added to the reaction mixture, and the organic layer was washed once with water (5 mL) and brine (5 mL). The organic layer was then dried (Na₂SO₄), filtered and concentrated. Silica gel column chromatography provided 0.021 g (48%) 1-(4-acetamidophenoxy)-6-O-acetyl-2,3-dideoxy 2,3-didehydro glucose 14 as a white solid.

Alternatively, 1-(4-acetamidophenoxy)-2,3-dideoxy 2,3-didehydro glucose 1 (0.281 g) was dissolved in 20 mL dry THF and 0.180 g pyridine and 0.160 g acetic anhydride and stirred at 0° C. for 4 hrs. The reaction was slow and thus was warmed to room temperature and stirred overnight. The reaction mixture was poured into 50 mL ethyl acetate and washed once each with 50 mL water, 25 mL 5% HCl, 25 mL saturated CuSO₄, 25 mL water, 25 mL saturated NaHCO₃ and 25 mL brine. The organic layer was then dried over Na₂SO₄, filtered, concentrated and purified by silica gel column chromatography (33% ethyl acetate to 75% ethyl acetate in hexanes) to provide 0.131 g (41%) 1-(4-acetamidophenoxy)-6-O-acetyl-2,3-dideoxy 2,3-didehydro glucose 14 as a white solid along with 0.012 g (4%) 1-(4-acetamidophenoxy)-4-O-acetyl-2,3-dideoxy 2,3-didehydro glucose and 0.100 g (27%) 1-(4'-acetamidophenoxy)-4,6-di-O-acetyl-2,3-dideoxy 2,3-didehydro glucose 6. ¹H NMR (300 MHz, CDCl₃) δ 2.07 (s, 3H), 2.16 (s, 3H), 2.57 (d, J=7.2 Hz, 1H, OH), 3.96 (ddd, J=2.4, 4.7, 9.3 Hz, 1H), 4.12 (dddd, J=2.4, 2.4, 7.2, 9.3 Hz, 1H), 4.19 (1H) and 4.57 (1H) (ABq, J_{AB}=12.4 Hz; the peaks at 4.19 are further split into d, J=2.4 Hz; the peaks at 4.57 are further split into d, J=4.7 Hz), 5.61 (s, 1H), 5.91 (1H) and 6.10 (1H) (ABq, J_{AB}=10.0 Hz; the peaks at 5.91 are split further into dd, J=2.4, 2.4 Hz), 7.05 (d, J=8.9 Hz, 2H), 7.25 (br s, 1H, NH), 7.39 (d, J=8.9 Hz, 2H); ¹³C NMR (75.5 MHz, CDCl₃) δ 20.9 (q), 24.2 (q), 63.5 (d), 63.7 (t), 71.0 (d), 93.7 (d), 117.7 (d, 2C), 122.0 (d, 2C), 125.5 (d), 132.7 (s), 134.4 (d), 154.0 (s), 169.3 (s), 171.8 (s).

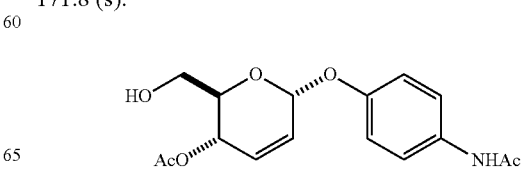

1-(4-acetamidophenoxy)-4-O-acetyl-2,3-dideoxy 2,3-didehydro glucose $^1$H NMR (300 MHz, CDCl$_3$) δ 2.12 (s, 3H), 2.15 (s, 3H), 2.21 (dd, J=5.5, 6.0 Hz, 1H, OH), 3.64 (1H) and 3.72 (1H) (ABq, J$_{AB}$=12.1 Hz; the 3.64 peaks are further split into dd, J=4.1, 6.0 Hz; the peaks at 3.72 are further split into d, J=5.5 Hz), 4.01 (ddd, J=2.5, 4.1, 9.6 Hz, 1H), 5.44 (dd, J=1.4, 9.6 Hz, 1H), 5.68 (s, 1H), 5.99 (1H) and 6.05 (1H) (ABq, J$_{AB}$=10.5 Hz; the peaks at 5.99 are further split into dd, J=1.4, 2.5 Hz), 7.04 (d, J=9.1 Hz, 2H), 7.26 (br s, 1H, NH), 7.40 (d, J=9.1 Hz, 2H).

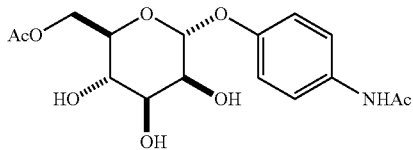

15

1-(4'-acetamidophenoxy)-6-O-acetyl-2,3-dideoxy 2,3-didehydro glucose 14 (2.50 g) was dissolved in 20 mL acetone and 5 mL water and 1.097 g N-methylmorpholone N-oxide and 0.247 g 4% OsO$_4$ in water added. The reaction was stirred at room temperature for 3 days, after which the reaction was judged complete by TLC. The reaction mixture was bound to a small (ca. 5 cc) amount of silica gel and silica gel column chromatography (ethyl acetate to 5% methanol in ethyl acetate) provided 2.200 g (80%) 1-(4'-acetamidophenoxy)-6-O-acetyl-mannose 15 as a white solid. $^1$H NMR (400 MHz, D$_2$O) δ 1.94 (s, 3H), 2.15 (s, 3H), 3.75 (dd, J=9.5, 9.9 Hz, 1H), 3.90 (dd, J=7.0, 9.9 Hz, 1H), 4.03 (dd, J=3.3, 9.5 Hz, 1H), 4.18 (dd, J=7.0, 12.1 Hz, 1H), 4.19 (d, J=3.3 Hz, 1H), 4.39 (d, J=12.1 Hz, 1H), 5.59 (s 1H), 7.12 (d, J=8.7 Hz, 2H), 7.37 (d, J=8.7 Hz, 2H); $^{13}$C NMR (75.5 MHz, D$_2$O) 22.8 (q), 22.8 (q), 66.3 (t), 69.5 (d), 72.5 (d), 73.1 (d), 73.6 (d), 100.9 (d), 120.3 (d, 2C), 125.8 (d), 126 (d), 134.0 (s), 154.9 (s), 175.1 (s), 176.5 (s).

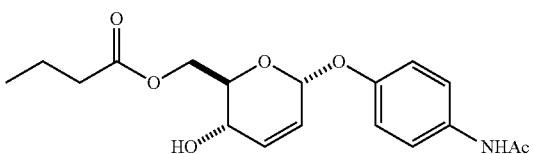

16

1-(4'-acetamidophenoxy)-2,3-dideoxy 2,3-didehydro glucose 1 (1.000 g) was dissolved in 6 mL THF and 1 mL DMF and 1.133 g (4 equivalents) pyridine and 0.623 g (1.1 equivalents) butyric anhydride were added and stirred for 3 hrs. The reaction mixture was poured into 100 mL ethyl acetate and washed with water (100 mL), saturated CuSO$_4$ (75 mL), saturated NaHCO$_3$ (100 mL) and brine (50 mL). The organic layer was then dried (Na$_2$SO$_4$), filtered, concentrated and purified by silica gel column chromatography (3:1 ethyl acetate/hexanes) to provide 0.500 g (40%) 1-(4'-acetamidophenoxy)-6-O-butyryl-2,3-dideoxy 2,3-didehydro glucose 16 as a white solid, along with a small amount (0.142 g, 9%) of 1-(4'-acetamidophenoxy)-4,6-O-dibutyryl-2,3-dideoxy 2,3-didehydro glucose and 0.057 g (5%) 1-(4'-acetamidophenoxy)-4-O-butyryl-2,3-dideoxy 2,3-didehydro glucose. $^1$H NMR (300 MHz, CDCl$_3$) δ 0.92 (dd, J=7.5, 7.5 Hz, 3H), 1.64 (ddq, J=7.5, 7.5, 7.5 Hz, 2H), 2.31 (dd, J=7.5, 7.5 Hz, 2H), 2.55 (d, J=6.6 Hz, 1H, OH), 3.95 (m, 1H), 4.08 (m, 1H), 4.19 (dd, J=2.2, 12.3 Hz, 1H), 4.59 (dd, J=4.2, 12.3 Hz, 1H), 5.61 (s, 1H), 5.90 (1H) and 6.00 (1H) (ABq, J$_{AB}$=10.2 Hz; the peaks at 5.90 are further split into dd, J=2.2, 2.2 Hz), 7.05 (d, J=8.8 Hz, 2H), 7.14 (br s, 1H, NH), 7.40 (d, J=8.8 Hz, 2H); $^{13}$C NMR (75.5 MHz, CDCl$_3$) δ 19.0 (q), 19.2 (t), 24.6 (q), 34.1 (t), 63.5 (t), 63.7 (d), 71.5 (d), 93.6 (d), 117.6 (d, 2C), 121.7 (d, 2C), 125.7 (d), 132.5 (s), 134.0 (d), 154.1 (s), 168.4 (s), 178.3 (s).

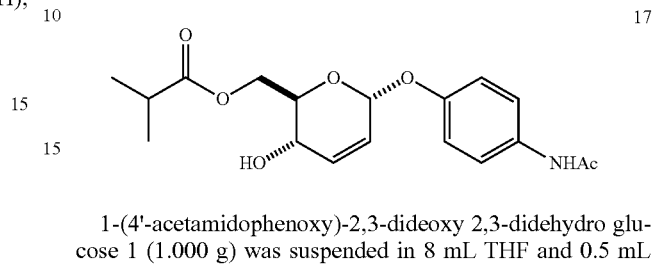

17

1-(4'-acetamidophenoxy)-2,3-dideoxy 2,3-didehydro glucose 1 (1.000 g) was suspended in 8 mL THF and 0.5 mL DMF and pyridine (1.133 g, 4 equivalents) and isobutyric anhydride (0.623 g, 1.1 equivalents) added. The reaction mixture was then stirred overnight, after which it was pouring into 200 mL ethyl acetate and washed once each with water (200 mL), saturated CuSO4 (100 mL), saturated sodium bicarbonate (200 mL) and brine (50 mL). The organic layer was then dried (Na2SO4), filtered, concentrated and purified by silica gel column chromatography (2:1 ethyl acetate/hexanes) to provide 1.981 g (55%) 1-(4'-acetamidophenoxy)-6-O-isobutyryl-2,3-dideoxy 2,3-didehydro glucose 17 as a white solid, along with 0.180 g (5%) 1-(4'-acetamidophenoxy)-4-O-isobutyryl-2,3-dideoxy 2,3-didehydro glucose and 0.164 g (11%) 1-(4'-acetamidophenoxy)-4,6-O-diisobutyryl-2,3-dideoxy 2,3-didehydro glucose. $^1$H NMR (300 MHz, D$_2$O) δ 1.13 (d, J=6.9 Hz, 3H), 1.15 (d, J=6.9 Hz, 3H), 2.17 (s, 3H), 2.51 (d, J=6.6 Hz, 1H, OH), 2.58 (qq, J=6.9, 6.9 Hz, 1H), (m, 1H), 4.06 (m, 1H), 4.20 (dd, J=2.4, 12.4 Hz, 1H), 4.57 (dd, J=4.7, 12.4 Hz, 1H), 5.61 (s, 1H), 5.90 (1H) and 6.11 (1H) (ABq, J$_{AB}$=10.2 Hz; the peaks at 5.90 are further spit into dd, J=2.4, 2.4 Hz), 7.06 (d, J=8.8 Hz, 2H), 7.09 (br s, 1H, NH), 7.39 (d, J=8.8 Hz, 2H); $^{13}$C NMR (100.6 MHz, D$_2$O) δ 19.0 (q), 19.1 (q), 24.5 (q), 34.0 (d), 63.5 (t), 63.6 (d), 71.4 (d), 93.6 (d), 117.6 (d, 3C), 121.8 (d, 2C), 125.7 (d), 132.5 (s), 134.1 (d), 154.1 (s), 168.5 (s), 178.3 (s).

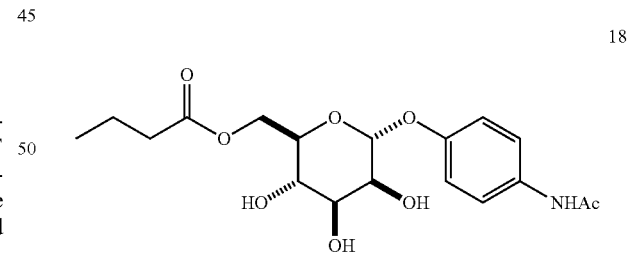

18

1-(4'-acetamidophenoxy)-6-O-butyryl-2,3-dideoxy 2,3-didehydro glucose 16 (0.500 g) and N-methylmorpholone N-oxide (0.25 g, 1.5 equivalents) were dissolved in 3 mL acetone and 3 mL water. OsO$_4$ (0.050 g 4% solution) was added and the reaction mixture stirred for 3 days. A small amount of silica gel (ca 2 cc) was then added and all of the solvent removed under reduced pressure. Silica gel column chromatography (3:1 ethyl acetate/hexanes to ethyl acetate) provided 0.510 g (93%) 1-(4'-acetamidophenoxy)-6-O-butyrylmannose 18 as a white solid. $^1$H NMR (300 MHz, D$_2$O) δ 0.73 (dd, J=7.3, 7.3 Hz, 3H), 1.31 (ddq, J=7.3, 7.3, 7.3 Hz, 2H), 2.03 (dd, J=7.3, 7.3 Hz, 2H), 2.09 (s, 3H), 3.67 (dd, J=9.5, 9.9 Hz, 1H), 3.80 (dd, J=8.1, 9.9 Hz, 1H), 3.98 (dd, J=3.3, 9.5 Hz, 1H), 4.08 (dd, J=8.1, 11.7 Hz, 1H), 4.11 (d, J=3.3 Hz, 1H), 4.39 (d, J=11.7 Hz, 1H), 5.49 (s, 1H), 6.97 (d, J=8.9 Hz, 2H), 7.31 (d, J=8.9 Hz, 2H); $^{13}$C NMR (75.5 MHz, D$_2$O) δ 15.5 (q), 20.44 (t), 25.5 (q), 38.3 (t), 66.4 (t), 69.8 (d), 72.4 (d), 73.1 (d), 73.8 (d), 100.5 (d), 120.2 (d, 2C), 125.3 (d, 2C), 135.0 (s), 154.6 (s), 174.9 (s), 178.8 (s).

19

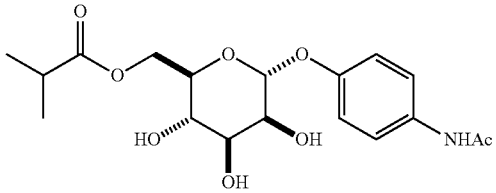

1-(4'-acetamidophenoxy)-6-O-isobutyryl-2,3-dideoxy 2,3-didehydro glucose 17 (0.600 g) and N-methylmorpholone N-oxide (0.303 g, 1.5 equivalents) were dissolved in 3 mL water and 3 mL acetone, 0.109 g 4% OsO$_4$ added and the reaction stirred for 3 days. A small amount of silica gel (ca. 2 cc) was added and all of the solvent removed under vacuum. Silica gel column chromatography (3:1 ethyl acetate/hexanes to ethyl acetate) provided 0.620 g (94%) 1-(4'-acetamidophenoxy)-6-O-isobutyrylmannose 19 as a white solid. $^1$H NMR (300 MHz, D$_2$O) δ 0.95 (d, J=6.9 Hz, 3H), 1.00 (d, J=6.9 Hz, 3H), 2.16 (s, 3H), 2.41 (qq, J=6.9, 6.9 Hz, 1H), 3.74 (dd, J=9.6, 9.6 Hz, 1H), 3.88 (dd, J=8.0, 9.6 Hz, 1H), 4.05 (dd, J=3.3, 9.6 Hz, 1H), 4.15 (dd, J=8.0, 11.9 Hz, 1H), 4.19 (d, J=3.3 Hz, 1H), 4.45 (d, J=11.9 Hz, 1H), 5.57 (s, 1H), 7.07 (d, J=8.8 Hz, 2H), 7.36 (d, J=8.8 Hz, 2H); $^{13}$C NMR (75.5 MHz, D$_2$O) δ 20.6 (q), 20.7 (q), 25.4 (q), 36.4 (d), 66.5 (t), 69.7 (d), 72.4 (d), 73.0 (d), 73.9 (d), 100.5 (d), 120.2 (d, 2C), 125.8 (d, 2C), 134.9 (s), 154.7 (s), 175.1 (s), 182.3 (s).

20

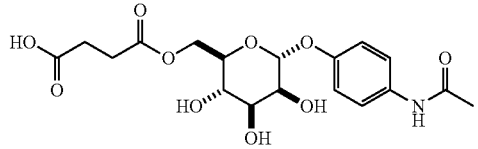

1-(4'-acetamidophenoxy)-2,3-dideoxy 2,3-didehydro glucose 1 (0.500 g) was dissolved in 5 mL THF, 1 mL DMF, and 0.566 g (4 equivalents) pyridine and 0.215 g (1.2 equivalents) succinic anhydride and the reaction was stirred overnight. Hexanes (5 mL) was added, stirred vigourously, and decanted off. This washing was repeated two more times, and the residual oil was pumped to dryness. NaHCO3 (300 mg, 2 equivalents) was dissolved in 2 mL water and added to the oil. After the oil was dissolved into the water solution, it was extracted three times with 1 mL ethyl acetate. Acetone (2 mL), N-methylmorpholone (0.421 g, 2 equivalents) and OsO$_4$ (0.46 g of a 4% solution) was added and the mixture warmed to 60° C. for 6 hrs. The reaction mixture was cooled to room temperature, silica gel (ca. 3 cc) added and the solvent removed under vacuum. Silica gel column chromatography (ethyl acetate to 25% methanol in ethyl acetate) provided the 0.170 g of the product 20 as an off-white solid $^1$H NMR (400 MHz, D$_2$O) δ 2.14 (s, 3H), 2.40-2.53 (m, 4H), 3.72 (dd, J=9.7, 9.7 Hz, 1H), 3.88 (dd, J=2.3, 9.7 Hz, 1H), 4.04 (dd, J=2.5, 9.7 Hz, 1 Hz), 4.14-4.19 (m, 2H), 4.45 (d, J=12.1 Hz, 1H), 5.62 (s, 1H), 7.12 (d, J=8.1 Hz, 2H), 7.39 (d, J=8.1 Hz, 2H); $^{13}$C NMR (100.6 MHz, D$_2$O) δ 25.4 (q), 31.4 (t), 31.6 (t), 57.1 (t), 66.6 (d), 69.6 (d), 72.4 (d), 73.1 (d), 73.7 (t), 100.5 (d), 120.4 (d, 2C), 126.2 (d, 2C), 134.8 (s), 154.7 (s), 175.5 (s), 177.1 (s), 179.6 (s).

21

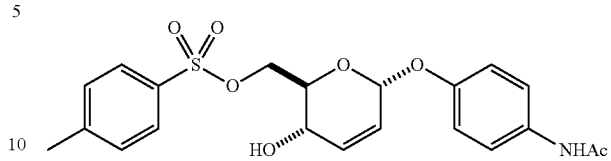

1-(4'-acetamidophenoxy)-2,3-dideoxy 2,3-didehydro glucose 1 (0.056 g) was dissolved in 0.5 mL pyridine and 0.050 g (1.3 equivalents) toluenesulfonyl chloride was added and stirred overnight. The reaction mixture was dissolved in 25 mL ethyl acetate and washed with 25 mL water, 15 mL saturated CuSO$_4$, 15 mL water, 15 mL NaHCO$_3$ and 15 mL brine. The organic layer was then dried over Na$_2$SO$_4$, filtered, concentrated and purified by silica gel column chromatography (1:2 ethyl acetate/hexanes to 2:1 ethyl acetate/hexanes) to provide 0.064 g (74%) 1-(4-acetamidophenoxy)-6-O-toluenesulfonyl-2,3-dideoxy 2,3-didehydro glucose 21 as a white solid and 0.015 g (13%) 1-(4'-acetamidophenoxy)-4,6-di-O-toluenesulfonyl-2,3-dideoxy 2,3-didehydro glucose. $^1$H NMR (300 MHz, CDCl$_3$) δ 2.13 (s, 3H), 2.43 (s, 3H), 2.84 (v br s, 1H, OH), 3.91 (ddd, J=1.9, 4.4, 9.6 Hz, 1H), 4.21 (1H) and 4.33 (1H) (ABq, J$_{AB}$=11.3 Hz, the peaks at 4.21 are further split into d, J=1.9 Hz; the peaks at 4.33 are further split into d, J=4.4 Hz), 4.24 (dd, J=2.5, 9.6 Hz, 1H), 5.49 (d, J=2.5 Hz, 1H), 5.85 (1H) and 6.06 (1H) (ABq, J$_{AB}$=10.2 Hz; the peaks at 5.85 are further split into dd, J=2.5, 2.5 Hz) 6.92 (d, J=9.1 Hz, 2H), 7.32 (d, J=8.1 Hz, 2H), 7.35 (d, J=9.1 Hz, 2H), 7.58 (br s, 1H, NH), 7.74 (d, J=8.1 Hz, 2H).

22

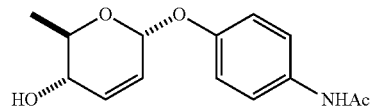

NaBH$_4$ (0.854 g) was suspended in 10 mL DMSO and heated until the NaBH$_4$ was dissolved. The solution was then cooled to near rt and 1-(4'-acetamidophenoxy)-6-O-toluenesulfonyl-2,3-dideoxy 2,3-didehydro glucose 21 (1.000 g) was added and the reaction mixture stirred for 3 days. The reaction was approximately 80% complete at this point; the reaction was heated to 90° C. for 1 hr, cooled to rt, and methanol (20 mL) added. Once the gas evolution stopped, the solution was concentrated, water (50 mL) added, and the aqueous solution extracted twice with 50 mL ethyl acetate. The combined organic layer was washed once with brine (25 mL), dried (Na2SO4), filtered and concentrated. The resultant oil was purified by silica gel column chromatography (20% acetone in hexanes) provide 1.291 g (56%) 1-(4'-acetamidophenoxy)-2,3,6-trideoxy 2,3-didehydro glucose 22 as a white solid. $^1$H NMR (300 MHz, CDCl$_3$) δ 1.31 (d, J=6.1 Hz, 3H), 2.16 (s, 3H), 3.83 (1H) and 3.91 (1H) (AB$_q$, J$_{AB}$=9.1 Hz; the peaks at 3.83 are further split into q, J=6.1 Hz), 5.90 (1H) and 6.07 (1H) (AB$_q$, J$_{AB}$=10.2 Hz), 7.05 (d, J=9.1 Hz, 2H), 7.40 (d, J=9.1 Hz, 2H); $^1$H NMR (300 MHz, d$_6$-acetone) δ 1.23 (d, J=5.8 Hz, 3H), 2.05 (s, 3H), 3.78-3.82 (m, 2H), 5.58 (d, J=2.8 Hz, 1H), 5.85 (1H) and 6.04 (1H) (AB$_q$, J$_{AB}$=9.9 Hz; the peaks at 5.85 are further split into dd, J=1.9, 2.8 Hz), 7.00 (d, J=9.1 Hz, 2H), 7.55 (d, J=9.1 Hz, 2H); $^{13}$C NMR (75.5 MHz, CDCl$_3$) δ 18.1 (q), 24.4 (q), 69.0 (d), 69.4 (d), 93.5 (d), 117.5 (d, 2C), 121.9 (d, 2C), 125.7 (d), 132.4 (s), 134.7 (d), 154.2 (s), 168.6 (s); $^{13}$C NMR (75.5 MHz, d$_6$-acetone) δ 18.3 (q), 24.1 (q), 69.4 (d), 69.5 (d), 94.3 (d), 118.0 (d, 2C), 121.2 (d, 2C), 125.8 (d), 134.8 (s), 136.1 (d), 154.4 (s), 168.6 (s).

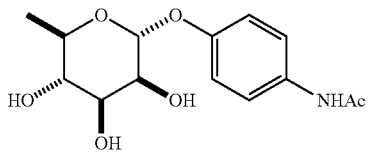

23

1-(4'-acetamidophenoxy)-2,3,6-trideoxy 2,3-didehydro glucose 22 (0.400 g) and N-methylmorpholone N-oxide (0.330 g, 1.85 equivalents) were dissolved in 6 mL acetone and 2 mL water and 54 mg 4% OsO4 added and stirred for 3 days. A small amount of silica gel (ca. 2 cc) was added and the solvent removed under vacuum. Silica gel column chromatography (ethyl acetate to 5% methanol in ethyl acetate) provided 0.400 g 1-(4'-acetamidophenoxy)-6-deoxymannose 23 as a white solid. $^1$H NMR (300 MHz, $D_2O$) δ; $^{13}$C NMR (75.5 MHz, $D_2O$) δ 1.23 (d, J=6.3 Hz, 3H), 3.53 (dd, J=9.6, 9.6 Hz, 1H), 3.80 (dq, J=6.3, 9.6 Hz, 1H), 3.99 (dd, J=3.4, 9.6 Hz, 1H), 4.16 (dd, J=1.6, 3.4 Hz, 1H), 5.51 (d, J=1.6 Hz, 1H), 7.11 (d, J=8.9 Hz, 2H), 7.35 (d, J=8.9 Hz, 2H); $^{13}$C NMR (75.5 MHz, $D_2O$) δ 19.3 (q), 25.3 (q), 72.2 (d), 72.7 (d), 72.8 (d), 74.7 (d), 101.1 (d), 120.4 (d, 2C), 126.5 (d, 2C), 134.6 (s), 155.4 (s), 175.6 (s).

Example VII

Pharmacokinetic and Brain Uptake of Glycosylated Acetaminophen with Perfalgan in Male Sprague Dawley Rats Following arrival at the testing facility, animals were assessed as to their general health and were acclimated for at least 3 days before being placed on study. Animals were group-housed during acclimation and individually housed during in-life. The animal room environment was controlled (temperature 18 to 26° C., relative humidity 30 to 70%, 12 hours artificial light and 12 hours dark) and temperature and relative humidity will be monitored daily. Animals were deprived of food overnight prior to dosing and fed Certified Rodent Diet approximately 4 hours post-dosing. Water was filtered and UV irradiated before provided to the animals ad libitum.

The dose solutions for acetaminophen and each of the analogs were prepared on the day of dosing and given to the animals within 2 hr after they are prepared. An appropriate amount of each analog was dissolved in sterile saline to obtain a 33 μmol/mL solution for acetaminophen, and analogs 5 and 8; and 66.3 μmol/mL for analogs 15, 18, 19, 20 and 23. A target dose for each analog given to each animal was 66.3 μmol/Kg. The dose formulations were each mixed by vortexing gently to allow for complete dissolution and the intravenous formulation was filtered before dosing. All formulations were protected from light once prepared. Two 50 μL aliquots per formulation were reserved for an initial dose validation. Dose formulation was assayed in duplicates for each dose using LC-UV with a calibration curve of 6 concentrations.

The dose formulation was administered intravenously via the jugular vein cannula for the animals in the pharmacokinetics study whereas the animals in brain-concentration study were dosed via tail vein injection.

For the pharmacokinetics study, three (3) animals per analog (and acetaminophen itself) were double cannulated using polyethylene tubing and Heparin Sodium (90-120 USP units)/glucose (50%) solutions as the lumen lock solution at both the carotid artery and jugular vein for the administration and blood sampling. For each analog being tested, approximately 0.3 mL blood was collected from the carotid artery via a catheter per sampling time point. After each time point blood collection, 0.3 mL of saline was added back immediately to keep the total volume a balance. All blood samples were transferred into polyethylene microcentrifuge tubes containing 90-120 USP units of sodium heparin as anti-coagulant and placed on wet ice until processed for plasma. Blood samples were processed for plasma by centrifugation (3,000 rpm for 5 minutes at 2 to 8° C.) within half an hour of collection and each transferred into a pre-labeled polyethylene microcentrifuge tube, quick-frozen in ethanol-dry ice bath, and stored frozen in a freezer set to maintain −70° C. or below until LC-MS/MS analysis.

For the brain uptake study, 2 animals were sacrificed at 30 min, 1, 2 and 4 hr postdose, with the individual brain concentrations at these times determined. Blood samples were collected via cardiac puncture while the animals are under anesthesia induced with a mixture of 70% $CO_2$ and 30% $O_2$. The whole brain was dissected, blotted on filter paper and weighed. The brain was then homogenized in 4 volumes of distilled water using ultrasonic processor. The homogenate process was performed on wet ice and the homogenate samples stored frozen in a freezer set to maintain −70° C. or below until LC-MS/MS analysis.

Plasma samples and brain homogenates were assayed using LC-MS/MS with internal standard, with the lower limit of quantification (LLOQ) of test article in plasma determined to be ≤3 ng/mL using a 0.05 mL plasma aliquot. Quality control samples (prepared in blank rat plasma and brain homogenates) were included in each analysis to ensure assay performance (acceptance criteria for QC are 4-6-20). Standard curve will be run in duplicates with minimum of 6 standards and at least ¾ of the total standards back calculated to within ±20% of their nominal concentrations. Plasma concentration versus time data were analyzed by non-compartmental approaches using the WinNonlin software program (version 5.2.1, Pharsight, Mountain View, Calif.), with calculation of the following parameters: $C_0$, $t_{1/2}$, CL, Vss, MRT, $AUC_{(0-t)}$, and $AUC_{(0-inf)}$. Concentrations less than lower quantification limit were not included in pharmacokinetic parameter analysis. Mean calculations of all pharmacokinetic parameters and their associated statistics were generated from un-rounded numbers.

REFERENCES

1. Klemke, E. R. et al. "Glycoside derivatives of acetaminophen," U.S. Pat. No. 5,693,767 (published Dec. 2, 1997).
2. Stache, U. et al. (1982) Synthesis of Cardenolide 3β-2',3'-Dideoxy-α,L-rhamnopyranosides, *Angewandte Chemie International Edition in English* 21, 547.
3. Stem, S. T. et al. (2005) Contribution of acetaminophen-cysteine to acetaminophen nephrotoxicity II. Possible involvement of the γ-glutamyl cycle, *Toxicol. Appl. Pharmacol.* 202, 160-171.
4. Mirochnitchenko, O. et al. (1999) Acetaminophen toxicity. Opposite effects of two forms of glutathione peroxidase, *J. Biol. Chem.* 274, 10349-10355.
5. Wuts, P. G M. and Greene, T. W. (2006) *Greene's Protective Groups in Organic Synthesis*, 4th ed., John Wiley & Sons, Inc., Hoboken, N.J.
6. Stahl, P. H. and Wermuth, C. G, (Eds.) (2002) *Handbook of Pharmaceutical Salts: Properties Selection and Use*, Verlag Helvetica Chimica Acta/Wiley-VCH, Zurich.

TABLE 1

| Acetaminophen analog | $D_2O$ solubility (mg/mL)[1] | $D_2O$ solubility (mM) | relative molar solubility |
|---|---|---|---|
| Acetaminophen[2] | 13 | 95 | 1 |
| Glucal 1 | 14 | 53 | 0.6 |
| 2,3-dideoxyglucose 12 | 9 | 31 | 0.3 |
| Mannose 8 | 51 | 164 | 1.8 |
| lactal 3 | 28 | 609 | 6.4 |
| Maltal 2 | 343 | 745 | 7.8 |
| glucose-mannose 5 | >621[3] | >1306 | >14 |
| 6-Ac-mannose 15 | 203 | 570 | 5.6 |
| 6-deoxy mannose 23 | 60 | 202 | 2.1 |
| mannose 6-butyrate 18 | 30 | 77 | 0.81 |
| mannose 6-isobutyrate 19 | 16 | 41 | 0.43 |

[1] Each sample was suspended in several mLs of $D_2O$ and stirred vigorously for 3 days. Each slurry was then filtered through a .2 μ syringe filter. A small amount of the filtrate was then measured (range of 0.1-0.3 mL in 0.1 mL increments) was then diluted with 50.4 mM DSS in $D_2O$ to a total volume of 0.6 mL (density measurements were also made and used to check the volume accuracy by using weight of the solution as a check). The resultant solution was then analyzed by $^1H$ NMR and the relative concentration of analog versus DSS measured, allowing for the solubility determination.
[2] The literature value of acetaminophen's solubility is 14 mg/ml.
[3] No solid was suspended in solution, all material was dissolved. Material crystallized from water would help in determining actual solubility.

TABLE 2

| | | Time to % hydrolysis (in days) | | |
|---|---|---|---|---|
| Compound | pD of sample | $t_{10\%}$ | $t_{25\%}$ | $t_{50\%}$ |
| glucal-acetaminophen 1 | pD 5 | 0.3 | 0.8 | 2.0 |
| | pD 6 | 2.25 | 6.25 | 17 |
| | pD 7 | 5.5 | 26 | 70 |
| maltal-acetaminphen 2 | pD 5 | 0.9 | 2.5 | 5.5 |
| | pD 6 | 6 | 20 | 50 |
| | pD 7 | 30 | 101 | |
| 2,3-dideoxyglucose acetaminophen 12 | pD 5 | 7 | 20 | 58 |
| | pD 6 | 48 | | |
| | pD 7 | | | |

TABLE 3

Pharmacokinetics Study Details

| Species | Male Sprague-Dawley rat | | | | | | | |
|---|---|---|---|---|---|---|---|---|
| Food | ad libitum | | | | | | | |
| Dose route | IV | | | | | | | |
| Compound ID | Acetaminoph | 5 | 8 | 15 | 18 | 19 | 20 | 23 |
| Molecular Formula | $C_8H_9NO_7$ | $C_{20}H_{19}NO_{12}$ | $C_{14}H_{19}NO_7$ | $C_{16}H_{23}NO_8$ | $C_{18}H_{25}NO_8$ | $C_{18}H_{25}NO_8$ | $C_{18}H_{28}NO_{10}$ | $C_{14}H_{19}NO_6$ |
| Nominal Dose(mg/kg)* | 10.0 | 31.5 | 20.7 | 23.5 | 25.4 | 25.4 | 27.3 | 19.7 |
| Nominal Dose(μmol/kg) | 66.2 | 66.3 | 66.1 | 66.1 | 66.3 | 66.3 | 66.0 | 66.3 |
| Adminisrated Dose (mg/kg) | 10.4 | 32.2 | 21.6 | 24.4 | 26.7 | 17.1 | 26.6 | 19.7 |
| Adminisrated Dose (umol/kg) | 68.8 | 67.7 | 69.0 | 68.8 | 69.6 | 44.7 | 64.5 | 66.3 |
| Formulation | 5.00 mg/mL, 33.1 umol/mL in sterile saline, solution | 15.75 mg/mL, 33.1 umol/mL in filter saline, clear solution | 10.35 mg/ml, 33.05 umol/mL in filtered saline, solution | 23.5 mg/mL, 66.1 umol/mL in water, clear solution | 25.4 mg/mL, 66.3 umol/mL in water, clear solution, pH 4-5 | 25.4 mg/mL, 66.3 umol/mL in water, clear solution, pH 4-5 | 27.3 mg/mL, 66.3 umol/mL in water, clear solution, pH 6 | 19.7 mg/mL, 66.3 nmol/mL in water, clear solution |
| Matrix | Plasma (EDTA-K2 as coagulant) for 5, 8, 15, 20, 23 Blood:ACN (including IS) = 1:3 (v:v)for 18, 19 | | | | | | | |

*equivalent to 10 mg/kg Acetaminophen

TABLE 4

| Time (h) | 5 | 8 | 15 | 18 | 19 | 20 | 23 |
|---|---|---|---|---|---|---|---|
| 0.000 | n.d. | n.d. | n.d. | n.d. | n.d. | n.d. | n.d. |
| 0.0333 | 1957 | 224400 | 53234 | 14551 | 14711 | 139420 | 87563 |
| 0.0833 | 4026 | 123106 | 16421 | 1675 | 3304 | 57413 | 44062 |
| 0.250 | 5404 | 50221 | 3594 | 62.9 | 676 | 27795 | 21784 |
| 0.500 | 297 | 18514 | 408 | n.d. | 78.2 | 7370 | 8577 |
| 1.00 | 478 | 3385 | 28.0 | n.d. | 8.62 | 889 | 3228 |
| 2.00 | 45.3 | 260 | n.d. | n.d. | n.d. | 59.6 | 632 |
| 4.00 | n.d. | 11.5 | n.d. | n.d. | n.d. | 25.9 | 146 |
| 6.00 | n.d. | 5.58 | n.d. | n.d. | n.d. | 11.8 | 42.7 |
| 8.00 | n.d. | n.d. | n.d. | n.d. | n.d. | 5.55 | 6.65 |
| 24.0 | n.d. | n.d. | n.d. | n.d. | n.d. | 31.5 | 40.0 |
| $C_0$ (nM) | 2494 | 335543 | 95834 | 43096 | 31070 | 217970 | 123477 |
| $t_{1/2}$ (h) | 1.32 | 0.659 | 0.220 | 0.0521 | 0.244 | 2.05 | 1.94 |
| $CL_p$ (mL/min/kg) | 759 | 24.7 | 78.7 | 345 | 203 | 22.7 | 24.9 |
| $Vd_{ss}$ (L/kg) | 26.8 | 0.349 | 0.800 | 1.56 | 1.77 | 0.549 | 1.58 |
| $AUC_{last}$ (nM · h) | 1566 | 44943 | 14229 | 3304 | 3678 | 51793 | 44017 |
| $AUC_{inf}$ (nM · h) | 1686 | 44948 | 14238 | 3308 | 3682 | 51857 | 44139 |
| $MRT_{inf}$ (h) | 0.653 | 0.236 | 0.170 | 0.0760 | 0.145 | 0.420 | 0.879 |
| $AUC_{inf}/AUC_{last}$ (%) | 106% | 100% | 100% | 100% | 100% | 100% | 100% |
| LLOQ (ng/mL) | 2.00 | 1.00 | 1.00 | 1.00 | 1.00 | 1.00 | 1.00 |
| LLOQ (nmol/L) | 4.21 | 3.19 | 5.63 | 5.22 | 2.61 | 2.42 | 3.36 |

TABLE 5

| Time (h) | aceta-minophen | Aceta-minophen from 5 | Aceta-minophen from 8 | Aceta-minophen from 15 | Aceta-minophen from 18 | Aceta-minophen from 19 | Aceta-minophen from 20 | Aceta-minophen from 23 |
|---|---|---|---|---|---|---|---|---|
| 0.000 | n.d. | n.d. | n.d. | n.d. | n.d. | n.d. | n.d. | n.d. |
| 0.0333 | 133854 | 10783 | 16627 | 14918 | 16468 | 12327 | 6525 | 1683 |
| 0.0833 | 89750 | 7895 | 17862 | 16612 | 11123 | 11357 | 8821 | 2719 |
| 0.250 | 45118 | 6845 | 15657 | 9950 | 7089 | 7023 | 6968 | 2631 |
| 0.500 | 23661 | 5672 | 10364 | 4237 | 2055 | 2000 | 3336 | 1524 |
| 1.00 | 5544 | 2505 | 2829 | 638 | 190 | 335 | 752 | 512 |
| 2.00 | 823 | 607 | 393 | 319 | 170 | 235 | 243 | 183 |
| 4.00 | 528 | 202 | 176 | 208 | 73.1 | 180 | 133 | 108 |
| 6.00 | 237 | 80.4 | 126 | 126 | 28.1 | 61.7 | 74.8 | 68.0 |
| 8.00 | 108 | 49.0 | 48.6 | 24.9 | n.d. | 18.4 | 93.4 | 35.4 |
| 24.0 | n.d. | n.d. | n.d. | n.d. | n.d. | n.d. | 62.5 | 12.9 |
| $C_0$ (nM) | 174733 | 13508 | 16925 | 14918 | 20122 | 12991 | 6525 | 1683 |
| $t_{1/2}$ (h) | 2.46 | 2.00 | 2.85 | 1.95 | 1.56 | 4.10 | 5.21 | 6.22 |
| $CL_p$ (mL/min/kg) | 26.9 | 138 | 87.8 | 76.7 | 115 | 116 | 112 | 238 |
| $Vd_{ss}$ (L/kg) | 1.06 | 10.2 | 5.25 | 5.51 | 5.18 | 9.44 | 21.5 | 47.6 |
| $AUC_{last}$ (nM·h) | 41031 | 8025 | 12616 | 14349 | 9521 | 9412 | 10406 | 4599 |
| $AUC_{inf}$ (nM·h) | 41231 | 8183 | 12718 | 14418 | 9587 | 9599 | 10794 | 4746 |
| $MRT_{inf}$ (h) | 0.661 | 1.23 | 0.979 | 1.20 | 0.751 | 1.35 | 3.45 | 338 |
| $AUC_{inf}/AUC_{last}$ (%) | 100% | 102% | 101% | 100% | 101% | 102% | 104% | 103% |
| LLOQ (ng/mL) | 1.00 | 1.00 | 1.00 | 2.00 | 2.00 | 2.00 | 2.00 | 1.00 |
| LLOQ (nmol/L) | 6.62 | 6.62 | 6.62 | 13.2 | 13.2 | 13.2 | 13.2 | 6.62 |

TABLE 6

| | Acetaminophen from acetaminophen | | | Acetaminophen from 5 | | | Acetaminophen from 8 | | |
|---|---|---|---|---|---|---|---|---|---|
| Time (h) | Plasma Mean (nmol/L) | Plasma Mean (nmol/L) | Ratio** | Plasma Mean (nmol/L) | Brain Mean (nmol/kg)* | Ratio** | Brain Mean (nmol/kg)* | Brain Mean (nmol/kg)* | Ratio** |
| 0.50 | 25767 | 17746 | 0.689 | 11114 | 2459 | 0.2213 | 19350 | 6831 | 0.353 |
| 1 | 4823 | 4846 | 1.00 | 3506 | 1606 | 0.4580 | 3639 | 2559 | 0.703 |
| 2 | 933 | 605 | 0.649 | 1555 | 796 | 0.5117 | 347 | 334 | 0.963 |
| 4 | 986 | 413 | 0.419 | 514 | 278 | 0.5419 | 192 | n.d. | n.d. |

*Brain concentration (nmol/Kg) = brain homogenate concentration (ng/mL) × 5 mL/g (dilution factor)/molecular weight × 1000
**Ratio = brain concentration (nmol/Kg)/plasma concentration (nmol/L)
N.D. = NOT DETERMINED

We claim:

1. A compound of the formula:

3. A compound of the formula:

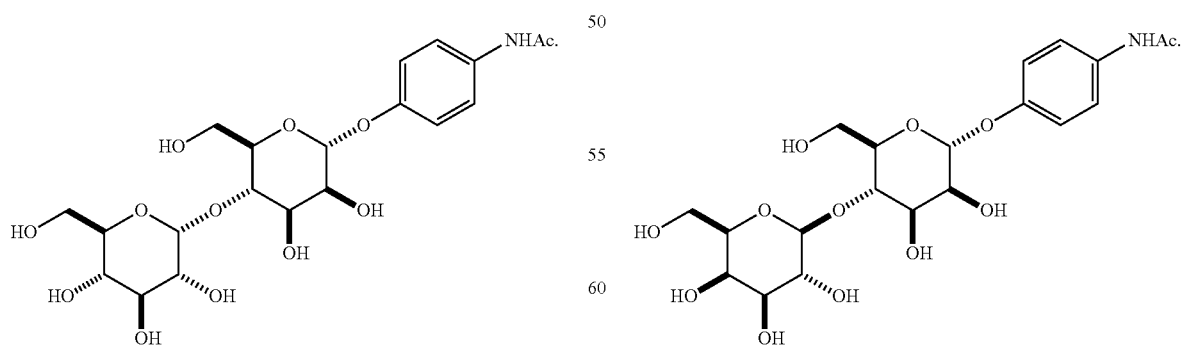

2. The compound of claim 1, further comprising a pharmaceutically effective carrier.

4. The compound of claim 3, further comprising a pharmaceutically effective carrier.

5. A compound of the formula:

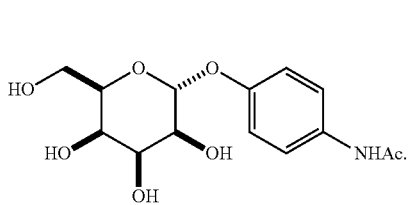

6. The compound of claim 5, further comprising a pharmaceutically effective carrier.

7. A compound of the formula:

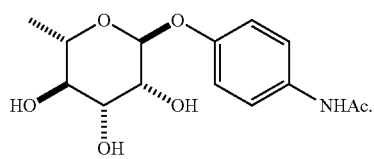 [SMILES: CC(=O)Nc1ccc(O[C@@H]2O[C@@H](C)[C@H](O)[C@@H](O)[C@H]2O)cc1]

8. The compound of claim 7, further comprising a pharmaceutically effective carrier.

9. A compound of the formula:

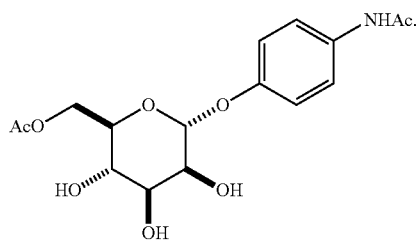

10. The compound of claim 9, further comprising a pharmaceutically effective carrier.

11. A compound of the formula:

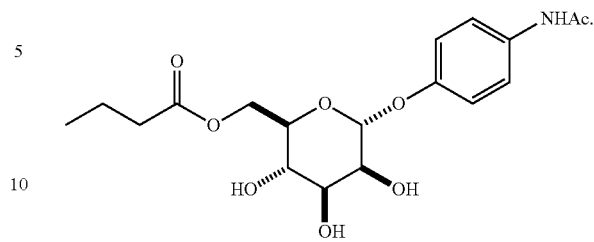

12. The compound of claim 11, further comprising a pharmaceutically effective carrier.

13. A compound of the formula:

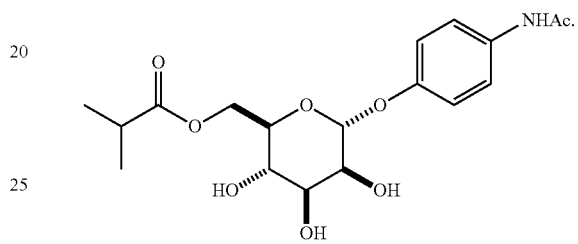

14. The compound of claim 13, further comprising a pharmaceutically effective carrier.

15. A compound of the formula:

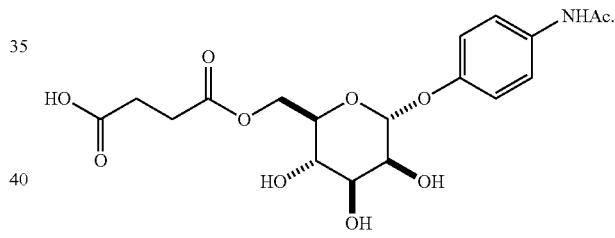

16. The compound of claim 15, further comprising a pharmaceutically effective carrier.

* * * * *